(12) United States Patent
Feuer et al.

(10) Patent No.: US 9,662,133 B2
(45) Date of Patent: *May 30, 2017

(54) JAWED TIP ASSEMBLY

(71) Applicant: TroCare LLC, Houston, TX (US)

(72) Inventors: Gerald Feuer, Atlanta, GA (US); Clark B. Foster, Mission Viejo, CA (US); Gerald Jay Sanders, Palo Alto, CA (US)

(73) Assignee: TROCARE LLC, Houston, TX (US)

( * ) Notice: Subject to any disclaimer, the term of this patent is extended or adjusted under 35 U.S.C. 154(b) by 126 days.

This patent is subject to a terminal disclaimer.

(21) Appl. No.: 14/262,566

(22) Filed: Apr. 25, 2014

(65) Prior Publication Data

US 2014/0235944 A1    Aug. 21, 2014

Related U.S. Application Data

(63) Continuation of application No. 13/280,233, filed on Oct. 24, 2011, now Pat. No. 8,708,889.

(51) Int. Cl.
| | |
|---|---|
| A61B 1/12 | (2006.01) |
| A61B 17/32 | (2006.01) |
| A61B 1/00 | (2006.01) |
| A61B 17/34 | (2006.01) |
| A61B 90/00 | (2016.01) |
| A61B 1/04 | (2006.01) |

(52) U.S. Cl.
CPC .. *A61B 17/320016* (2013.01); *A61B 1/00087* (2013.01); *A61B 1/126* (2013.01); *A61B 17/3417* (2013.01); *A61B 17/3478* (2013.01); *A61B 90/37* (2016.02); *A61B 1/00096* (2013.01); *A61B 1/00177* (2013.01); *A61B 2017/3454* (2013.01)

(58) Field of Classification Search
CPC ....... A61B 1/0008; A61B 1/126; A61B 1/127; A61B 17/34
USPC .... 600/104, 156–158, 219–223; 604/164.01, 604/267; 606/185
See application file for complete search history.

(56) References Cited

U.S. PATENT DOCUMENTS

| | | |
|---|---|---|
| 4,919,113 A | 4/1990 | Sakamoto |
| 5,339,800 A | 8/1994 | Wiita et al. |
| 5,382,297 A | 1/1995 | Valentine et al. |

(Continued)

FOREIGN PATENT DOCUMENTS

| | | |
|---|---|---|
| CN | 101069633 A | 11/2007 |
| EP | 1210904 A2 | 6/2002 |

(Continued)

OTHER PUBLICATIONS

Notification of Transmittal of The International Search Report and The Written Opinion of the International Searching Authority, or the Declaration for International Application No. PCT/US2012/061741; mailed May 23, 2013.

(Continued)

*Primary Examiner* — Timothy J Neal
(74) *Attorney, Agent, or Firm* — POLSINELLI PC

(57) ABSTRACT

A tip assembly is presented herein. The tip assembly can have a member having a first end and a second end. The first end of the member can be open. The first end also can allows an implement to be inserted. The tip assembly also includes a jaw hingedly coupled to the second end of the member.

16 Claims, 16 Drawing Sheets

(56) References Cited

U.S. PATENT DOCUMENTS

| | | |
|---|---|---|
| 5,392,766 A | 2/1995 | Masterson et al. |
| 5,419,309 A | 5/1995 | Biehl |
| 5,514,084 A | 5/1996 | Fisher |
| 5,916,232 A | 6/1999 | Hart |
| 6,110,103 A | 8/2000 | Donofrio |
| 6,126,592 A | 10/2000 | Proch et al. |
| 6,286,179 B1 | 9/2001 | Byrne |
| 6,354,992 B1 | 3/2002 | Kato |
| 6,409,657 B1 | 6/2002 | Kawano |
| 6,447,446 B1 | 9/2002 | Smith et al. |
| 6,595,915 B2 | 7/2003 | Akiba |
| 6,638,214 B2 | 10/2003 | Akiba |
| 6,699,331 B1 | 3/2004 | Kritzler |
| 6,712,757 B2 | 3/2004 | Becker et al. |
| 6,755,782 B2 | 6/2004 | Ogawa |
| 6,770,026 B2 | 8/2004 | Kan et al. |
| 6,923,759 B2 | 8/2005 | Kasahara et al. |
| 7,018,384 B2 | 3/2006 | Skakoon |
| 7,547,314 B2 | 6/2009 | Kadykowski |
| 7,771,384 B2 | 8/2010 | Ravo |
| 7,811,228 B2 | 10/2010 | Adams |
| 7,833,155 B2 | 11/2010 | Torii |
| 7,959,561 B2 | 6/2011 | Akui et al. |
| 8,708,889 B2 * | 4/2014 | Feuer .................. A61B 1/00087 600/109 |
| 2002/0065450 A1 | 5/2002 | Ogawa |
| 2002/0169362 A1 | 11/2002 | Kan et al. |
| 2004/0044348 A1 | 3/2004 | Skakoon |
| 2006/0079925 A1 | 4/2006 | Kerr |
| 2007/0225566 A1 | 9/2007 | Kawanishi |
| 2008/0188715 A1 | 8/2008 | Fujimoto |
| 2008/0200765 A1 | 8/2008 | Mondschein |
| 2009/0105543 A1 | 4/2009 | Miller |
| 2009/0234193 A1 | 9/2009 | Weisenburgh, II et al. |
| 2009/0240111 A1 | 9/2009 | Kessler et al. |
| 2009/0250081 A1 | 10/2009 | Gordin et al. |
| 2009/0253964 A1 | 10/2009 | Miyamoto |
| 2009/0264703 A1 | 10/2009 | Pribanic |
| 2009/0270686 A1 | 10/2009 | Duke |
| 2010/0010310 A1 | 1/2010 | Weisenburgh, II et al. |
| 2010/0012152 A1 | 1/2010 | Hansen |
| 2010/0022958 A1 | 1/2010 | Moreno, Jr. et al. |
| 2010/0174144 A1 | 7/2010 | Hsu et al. |
| 2011/0046439 A1 | 2/2011 | Pamnani et al. |
| 2011/0152776 A1 | 6/2011 | Hartoumbekis et al. |

FOREIGN PATENT DOCUMENTS

| | | |
|---|---|---|
| EP | 1854421 A2 | 11/2007 |
| EP | 2111782 A2 | 10/2009 |
| WO | 9212680 | 8/1992 |
| WO | 9623536 | 8/1996 |
| WO | 01/89371 A1 | 11/2001 |
| WO | 2011/085366 A1 | 7/2011 |

OTHER PUBLICATIONS

International Search Report for for International Application No. PCT/US2012/061741; mailed May 23, 2013.
Written Opinion of the International Searching Authority for International Application No. PCT/US2012/061741; mailed May 23, 2013.
Notice of Allowance for U.S. Appl. No. 13/280,233 dated Dec. 13, 2013.
Non-Final Office Action for U.S. Appl. No. 13/280,233 dated Jul. 31, 2013.
Chinese Office Action; CN Application No. 2012800642252; mailed Feb. 24, 2016.
English translation of Chinese Office Action; CN Application No. 2012800642252; mailed Feb. 24, 2016.
English abstract of CN101069633; retrieved on Aug. 12, 2016; www.espacenet.com.

* cited by examiner

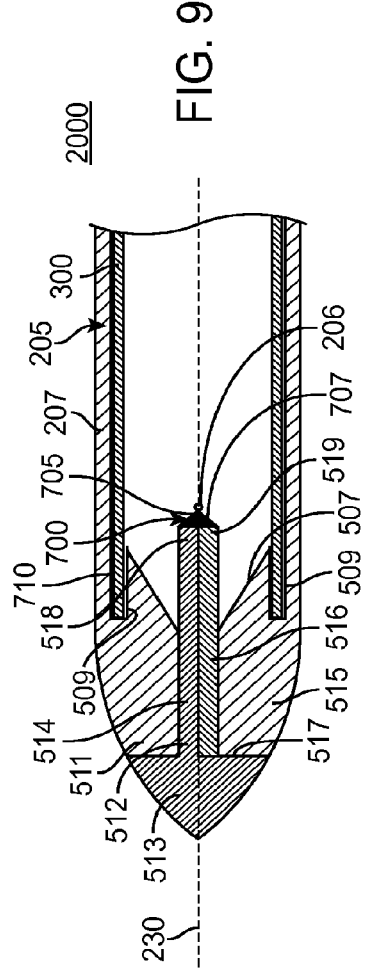
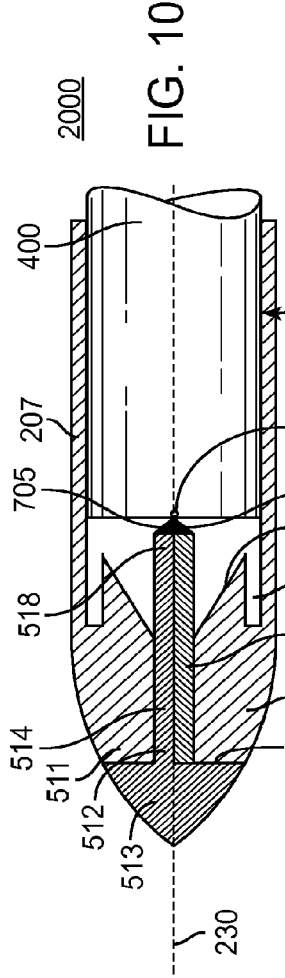
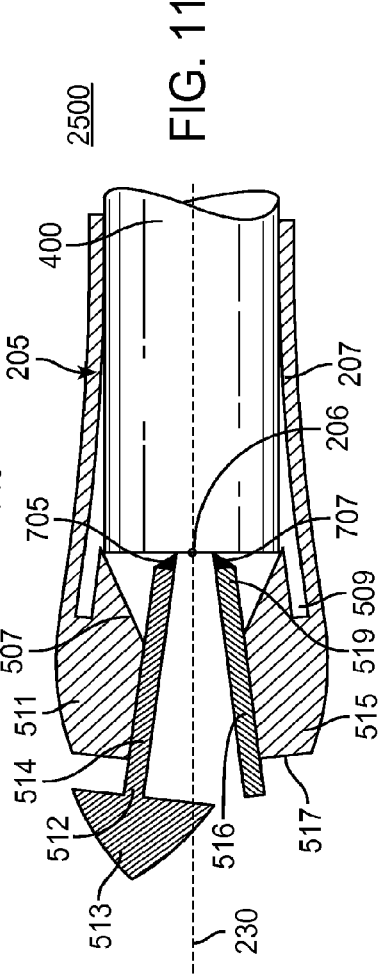
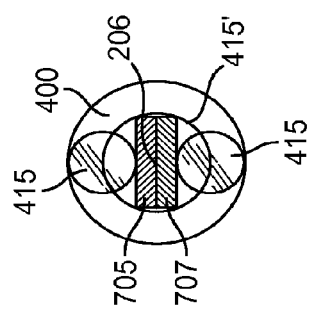
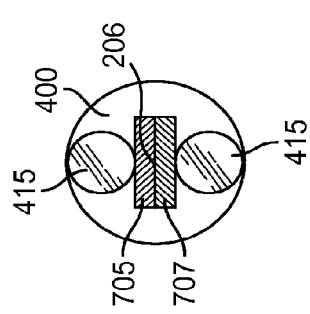
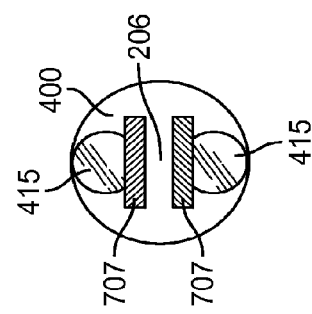
FIG. 9
FIG. 10
FIG. 11

JAWED TIP ASSEMBLY

CROSS-REFERENCE TO RELATED APPLICATIONS

This application is a continuation application of U.S. patent application Ser. No. 13/280,233, filed Oct. 24, 2011, which is incorporated by reference.

FIELD OF TECHNOLOGY

The present disclosure relates generally to trocar devices, and more specifically, to jawed trocar assemblies which can be utilized in surgical procedures.

BRIEF DESCRIPTION OF THE DRAWINGS

Implementations of the present application will now be described, by way of example only, with reference to the attached Figures, wherein:

FIGS. 9-13 are cross-sectional views of an exemplary embodiment of a jawed trocar assembly, in accordance with the present disclosure, having a scope cleaner mechanism coupled thereto, illustrating several positions of the scope cleaner mechanism against an endoscope inserted into the jawed trocar assembly to clean debris from the surface of the endoscope;

DETAILED DESCRIPTION

Figure 1:
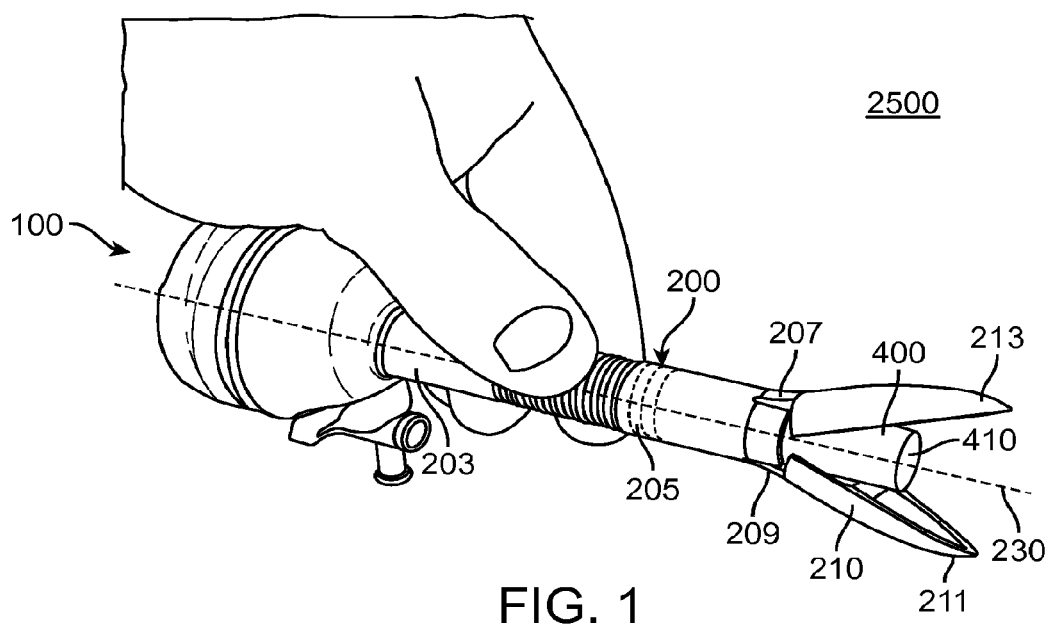
FIG. 1 is a perspective view of an endoscopic tool assembly in accordance with an exemplary embodiment of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the implementations described herein. However, it will be understood by those of ordinary skill in the art that the implementations described herein can be practiced without these specific details. In other instances, methods, procedures and components have not been described in detail so as not to obscure the related relevant feature being described. Also, the description is not to be considered as limiting the scope of the implementations described herein.

Several definitions that apply throughout this document will now be presented. The phrase "coupled" is defined as connected, whether directly or indirectly through intervening components and is not necessarily limited to physical connections.

Medical procedures performed within the body cavity of a patient are typically achieved through narrow tubes or cannulas inserted through a small entrance incision in the skin of the patient. Typically, the cannula is extended into the patient's body through the entrance incision to provide an access port. The access port allows the surgeon to insert a number of different medical implements therethrough. For example, the medical implements can be inserted through the cannula or a trocar to access portions of the body cavity that are far removed from the incision. Medical procedures which utilize cannulas and/or trocars can include endoscopic procedures in which an endoscope is inserted into the cavity to provide the surgeon with a view of the interior cavity of the patient, laparoscopic procedures, colonoscopic procedures, and other minimally invasive procedures which are performed via small incisions in the skin of a patient. Many of these procedures are often performed remotely from the incision. Consequently, application of the medical implements can be complicated by a reduced field of view and/or a reduced tactile feedback from the surgeon at the proximal end of the medical implement.

A trocar assembly in accordance with the present disclosure can include a hollow elongate member and a jaw. The hollow elongate member can have a first end a second end. The first end can be open and configured to receive an implement insertable therethrough. The jaw can be hingedly coupled to the second end of the hollow elongate member.

The jaw can be adapted to penetrate at least one layer of a body tissue. For example, the jaw can be adapted to penetrate at least one layer of a body tissue. The trocar assembly can have a first position and a second position. The first position can be a rest position wherein the jaw is substantially parallel to a longitudinal axis of the hollow elongate member. The second position can be an expanded position wherein the jaw is rotated such that an end of the jaw is positioned radially away from the longitudinal axis. In the event the implement is inserted through the hollow elongate member, when the trocar assembly is placed in the second position, the implement can be protrudable therefrom. For example, in the event the implement is inserted and received within the hollow elongate member, the trocar assembly can be transitionable into the second position. For example, when the implement is longitudinally advanced through the hollow elongate member to protrude out from the second end of the hollow elongate member, the jaw can be rotated such that the end of the jaw is positioned radially away from the longitudinal axis of the hollow elongate member, thereby placing the trocar assembly in the second position. In this second position, as the implement is protrudable from the second end of the hollow elongate member and from the end of the jaw, the implement can engage portions of a body cavity of a patient to perform medical procedures within the body cavity.

Other configurations and arrangements will be described below in relation to illustrated implementations. One of ordinary skill would appreciate that the elements from the illustrated implementations can be optionally included, combined, omitted, and arranged in various combinations to achieve the described benefits of the presently disclosed notification device. It will also be appreciated that while FIGS. 4-23 illustrate distal ends of the jawed trocar assembly, these views are merely for illustration, and those of ordinary skill in the art will appreciate that the length of the jawed trocar assembly can vary from views illustrated therein.

Figure 3:
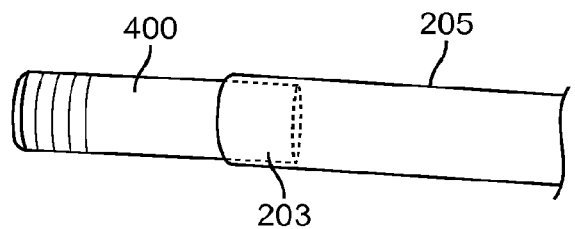
FIG. 3 is a partial side view of a jawed trocar assembly illustrating an insertion of an implement into the jawed trocars in accordance with an exemplary embodiment of the present disclosure having an implement inserted therethrough.

FIG. 1 is perspective view of an exemplary embodiment of a medical implement assembly having a trocar assembly in accordance with the present disclosure. The medical implement assembly 100 in FIG. 1 can include a trocar assembly 200 and an implement 400. For example, in FIG. 1, the implement 400 is an endoscope. However, the implement 400 can also be a laparoscope, an endoscopic stapler, a suctioning device, a fluid line, or other implement. The trocar assembly 200 can include a hollow elongate member 205 having a first end 203 and a second end 209. The first end 203 can be the proximal end which is closest to the surgeon during medical procedures. The implement 400 can be insertable through the first end 203 of the hollow elongate member 205, as shown in FIG. 3. The second end 207 can be the distal end which is inserted into the body cavity of a patient for medical procedures. The second end 207 can also have a circumference 209. As illustrated in FIG. 1, the trocar assembly 200 can include at least one jaw 210 coupled to the second end 209 of the elongate member 205. For example, in FIG. 1, the at least one jaw 210 is hingedly coupled to a circumference 209 of the second end 207 of the hollow elongate member 205. The trocar assembly 200 can have a first position 2000 (shown in FIG. 4) to a second position 2500 (shown in FIG. 1). In the second position 2500, shown as an expanded position in FIG. 1, the at least one jaw 210 can be rotated such than an end 213 of the at least one jaw 210 is positioned radially away from the longitudinal axis 230 of the hollow elongate member 205. Those of ordinary skill in the art will appreciate that while FIG. 1 illustrates the at least one jaw 210 rotates radially away from the longitudinal axis, the at least one jaw 210 can rotate along an axis of rotation offset from the longitudinal axis of the hollow elongate member 205. For example, the at least one jaw 210 can be hinged to the circumference of the hollow elongate member 205 such that the at least one jaw 210 can swing away from the longitudinal axis 230 of the hollow elongate member 205, similar to the way a door moves on a door hinge.

In FIG. 1, the at least one jaw 210 includes a pair of jaws. Each of the pair of jaws 210 can be hingedly coupled to the second end 207 of the hollow elongate member 205. For example, in FIG. 1, each jaw is hingedly coupled to the circumference 209 of the second end 207 of the hollow elongate member 205. Also illustrated in FIG. 1, the pair of jaws 210 can be coupled to the hollow elongate member 205 such that each jaw 210 is opposite to the other. In at least one embodiment, at least one of the pair of jaws 210 can have a penetrating surface 211 adapted to penetrate through at least one layer of the body tissue. In another embodiment, both of the jaws 210 can have a penetrating surface 211. The penetrating surface 211 can be an abrasive surface, a smooth surface, a blade, a razor, a sharp edge, or other surface which allows the at least one jaw 210 to penetrate through at least one layer of body tissue. Further details as to the first position 2000 and second position 2500 of a trocar assembly 200 having a pair of jaws 210 will be discussed below with respect to FIGS. 4 and 5. In this second position 2500, the implement 400 can protrude from the second end 207 of the hollow elongate member, through the jaws 210, and out from the jaws 210. For example, in the second position 2500, the distal end 410 of the implement 300 can protrude form the end 213 of the at least one jaw 210.

In FIG. 1, the at least one jaw 210 can be configured to penetrate (for example, make an incision) through at least one layer of a body tissue. Those of skill will appreciate that in order to penetrate at least one layer of body tissue, the at least one jaw 210 of the trocar assembly 200 can be substantially rigid to allow pressure to be placed on the trocar assembly 200 to penetrate the at least one layer of body tissue. For example, the at least one jaw 210 can be made of a rigid material. For example, the jaw can be made of a hard plastic, metal, composite material, or other material that does not substantially deform when pressure is applied to the at least one jaw 210 to penetrate through at least one layer of body tissue. In another embodiment, the at least one jaw 210 can be made of a semi-deformable material, such as a pliable plastic or other semi-deformable material that does not substantially deform when pressure is applied to the at least one jaw 210 to penetrate through the at least one layer of body tissue. Those of ordinary skill in the art will appreciate that the at least one jaw 210 can be made of a biologically-safe material, as the at least one jaw 210 is insertable into a body cavity of patient. Some examples of biologically-safe material include but are not limited to polycarbonate and polysuphone.

Figure 2:
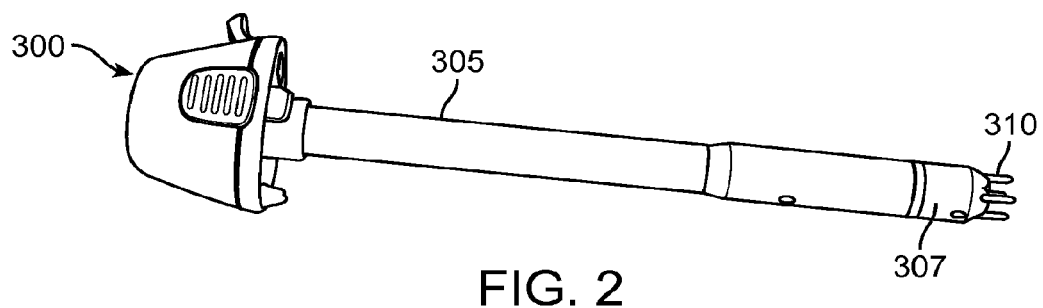
FIG. 2 is a perspective view of a locking member for a jawed trocar assembly in accordance with an exemplary embodiment of the present disclosure.

In another embodiment, the at least one jaw 210 can be made of a deformable plastic, but the at least one jaw 210 can be couplable to a locking member 300 (shown in FIG. 2) which when coupled to the at least one jaw 210, provides the at least one jaw 210 with a rigidity that reduces the deformation of the at least one jaw 210 when pressure is applied thereto to penetrate through the at least one layer of body tissue. For example, in an embodiment where the at least one jaw 210 includes a pair of jaws, a locking member 300 (shown in FIG. 2) can be coupled to the pair of jaws to maintain the pair of jaws in the rest position 2000 (shown in FIG. 4) and to provide the pair of jaws with sufficient rigidity such that when pressure is placed on the jaws 210 to penetrate through a layer of body tissue, the pair of jaws 210 will not deform. FIG. 2 illustrates an exemplary locking member 300 which can be couplable to a pair of jaws. For example, in FIG. 2, the locking member 300 can include a rod 305. The rod 305 can be a tube, a hollow tube, a cylindrical member, a hollow cylindrical member, a wire, or any other structure or member which can be coupled to the hollow elongate member 205 and can maintain the jaw in the rest position. In FIG. 2, the rod 305 can be insertable through the hollow elongate member 205. At least one protrusion 310 can coupled to an end 307 of the rod 305. For example, the at least one protrusion 310 can be welded, screwed, glued, or otherwise attached to the rod 305. In other embodiments, the at least on protrusion 310 can be formed at the end of the rod 305.

Figure 8:
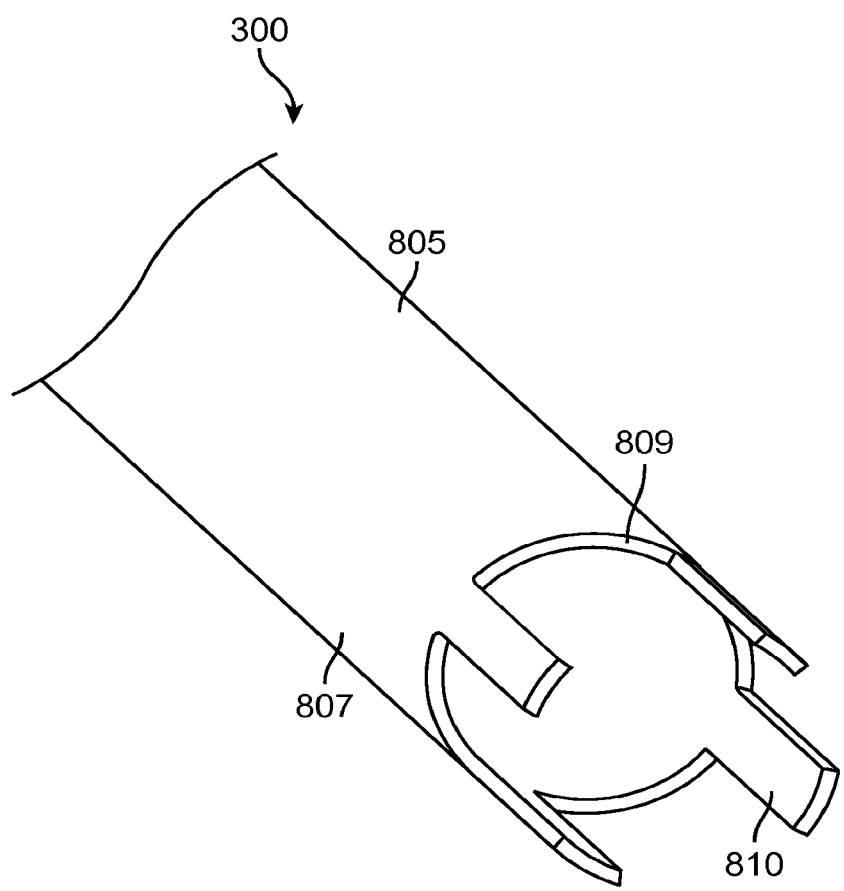
FIG. 8 is a perspective view of a locking member configured for engagement with the jawed trocar assembly to maintain the jawed trocar assembly in the rest position in accordance with the present disclosure.

In FIG. 2, the at least one protrusion 310 can be coupled to the end 307 of the rod 305 that is adjacent the at least one jaw 210 coupled to the hollow elongate member 205, in the event the locking member 300 is inserted into the hollow elongate member. In FIG. 2, the locking member 300 includes four protrusions 310. However, those of ordinary skill in the art will appreciate that any number of protrusions 310 can be implemented. Each of the protrusions 310 can matingly engage with a corresponding recess (not shown) formed in at least one of the jaws 210 illustrated in FIG. 1. In the event the locking member 100 is inserted into the hollow elongate member 205 and at least one of the protrusions 310 matingly engages the corresponding recess, the jaws 210 can be locked or maintained in the rest position 2500, thereby allowing pressure to be placed on the jaws 210 to penetrate through at least one layer of body tissue, without substantially deforming the jaws 210. The locking member 300 can be removable from the hollow elongate member 205, thereby disengaging the at least one protrusion 310 from the jaws 210. In the event the locking member 300 is removed from the hollow elongate member 205, the trocar assembly 100 can be transitionable between a first position (for example, rest position) and a second position (for example, and expanded position). FIG. 8 illustrates another embodiment of a locking member 300. In FIG. 8, the locking member 300 includes a hollow cylindrical member 805 having an end 807. At least one tab 810 can be coupled to the end 807 of the hollow cylindrical member 805. For example, as illustrated in FIG. 8, a plurality of tabs 810 are formed along the circumference 809 of the end 807 of the hollow cylindrical member 805. Similar to the protrusions of the locking member 300 illustrated in FIG. 2, when the hollow cylindrical member 805 is inserted in the hollow elongate member 205 of the trocar assembly 200, the plurality of tabs 805 can engage recesses 509 (shown in FIGS. 9-13) formed in the at least one jaw 210 to maintain the trocar assembly 200 in a rest position 2000. For example, by maintaining the jaws 210 in the rest position 2000.

Figure 4:
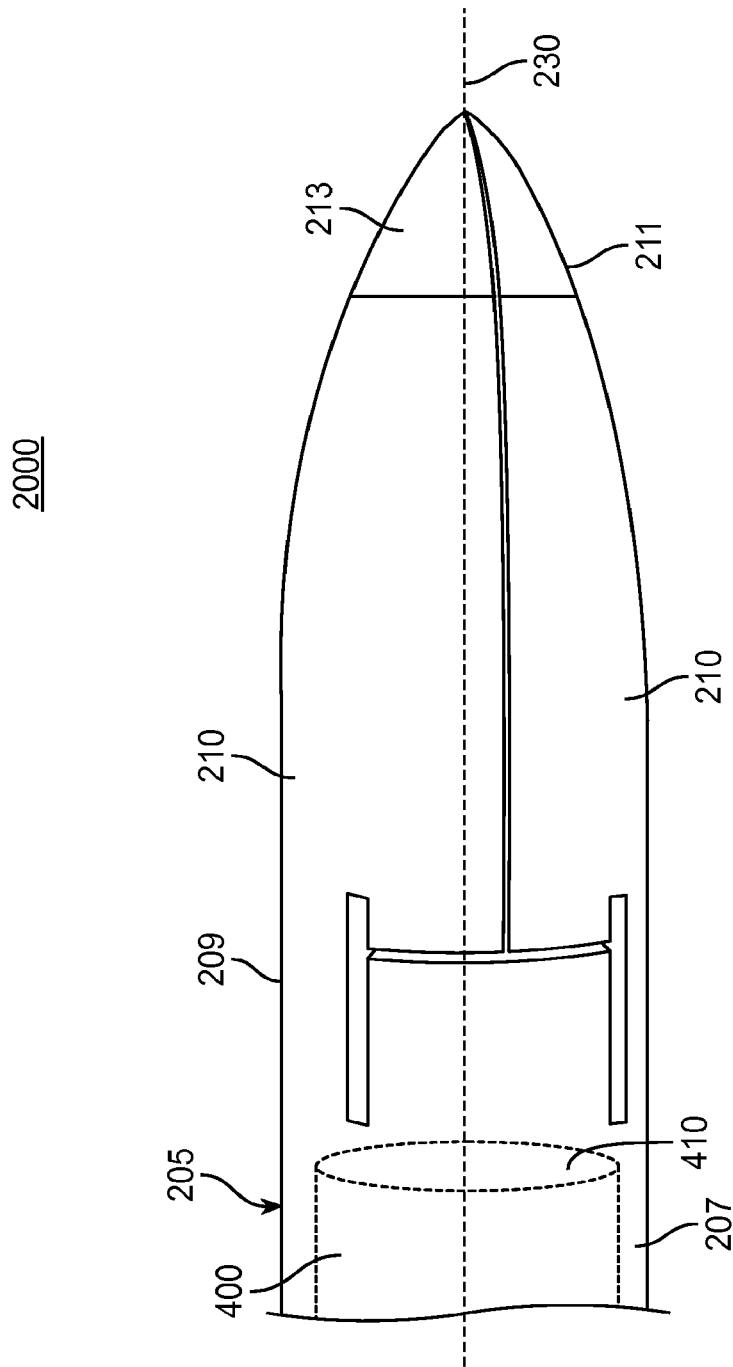
FIG. 4 is a side view of a second end of a jawed trocar assembly in a first position (for example, a rest position) in accordance with an exemplary embodiment of the present disclosure.
Figure 5:
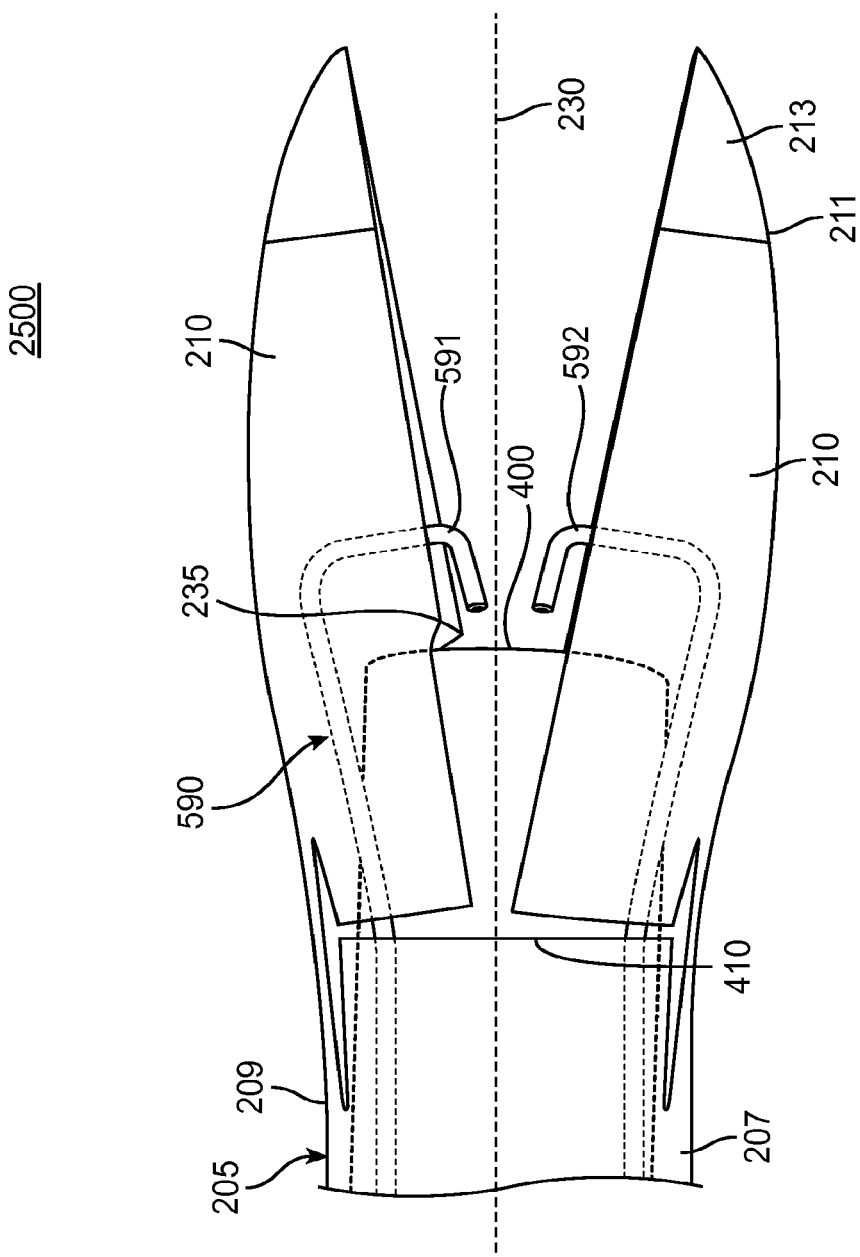
FIG. 5 is a side view of a second end of a jawed trocar assembly in a second position (for example, an expanded position) in accordance with an exemplary embodiment of the present disclosure.

FIGS. 4 and 5 illustrate a partial view of the at least one jaw 210 illustrated in the trocar assembly 100 of FIG. 1. FIG. 4 illustrates the at least one jaw 210 the at least one jaw 210 in a first position 2000 that is a rest position. For example, in FIG. 4, the at least one jaw 210 the at least one jaw 210 is a pair of jaw 210. In the first position 2000, the pair of jaws 210 are each substantially parallel to the longitudinal axis of the hollow elongate member 205. Also illustrated in FIG. 4, in the first position 2000, the pair of jaws 210 are positioned with respect to one another such that the ends 213 of each of the jaws 210 form a substantially conical contour adapted to penetrate the layer of the body tissue. The first position 2000 can be a position in which an implement 400 has been inserted through the cavity of the hollow elongate member 205 but has not been advanced therethrough to protrude from the second end 207 of the hollow elongate member 205. When the implement 400 has been inserted through the cavity of the hollow elongate member 205 and is advanced therethrough such that the implement 400 begins to protrude out from the second end 207 of the hollow elongate member 205 and begins to engage an inner surface 235 (shown in FIG. 5) of at least one of the jaws 210, the trocar assembly 100 can be transitioned into the second position 2500.

FIG. 5 illustrates a partial view of the trocar assembly 100 as the trocar assembly is transitioning into the second position 2500. In the second position 2500, each of the jaws of the pair of jaws 210 can be rotated such that the ends 213 of each jaw 210 are positioned radially away from the longitudinal axis 230. In this second position 2500, the implement 400 can be protrudable therefrom to perform medical procedures within the body cavity. As illustrated in FIG. 5, the end 410 of the implement 400 can engage an interior surface 235 of at least one of the jaws 210 as the implement is advanced through the hollow elongate member 205. As the implement 400 is further advanced through the hollow elongate member 205 to protrude out from the second end 207, the end 410 of the implement 400 can apply a force against the interior surface 235 of at least one of the jaws 210 to permit the rotation of at least one of the jaws 210 about the second end 207 of the hollow elongate member 205 to displace or position the ends 213 of the jaws 210 radially away from the longitudinal axis 230 of the hollow elongate member 205. The further the implement 400 is advanced through hollow elongate member 205, the jaws 210 are further rotated, and the radial distance between the ends 213 of the jaws 210 from the longitudinal axis 230 of the hollow elongate member 205 is increased. The implement 400 can be advanced through the hollow elongate member 205 and through the jaws 210 such that the end 410 of the implement 400 can protrude a distance away from the ends 213 of the jaws 210. As the implement 400 can protrude a distance away from the ends 213 of the jaws 210, the implement 400 can be manipulated for medical procedures within the patient's body cavity without substantial interference from the jaws 210.

Figure 6:
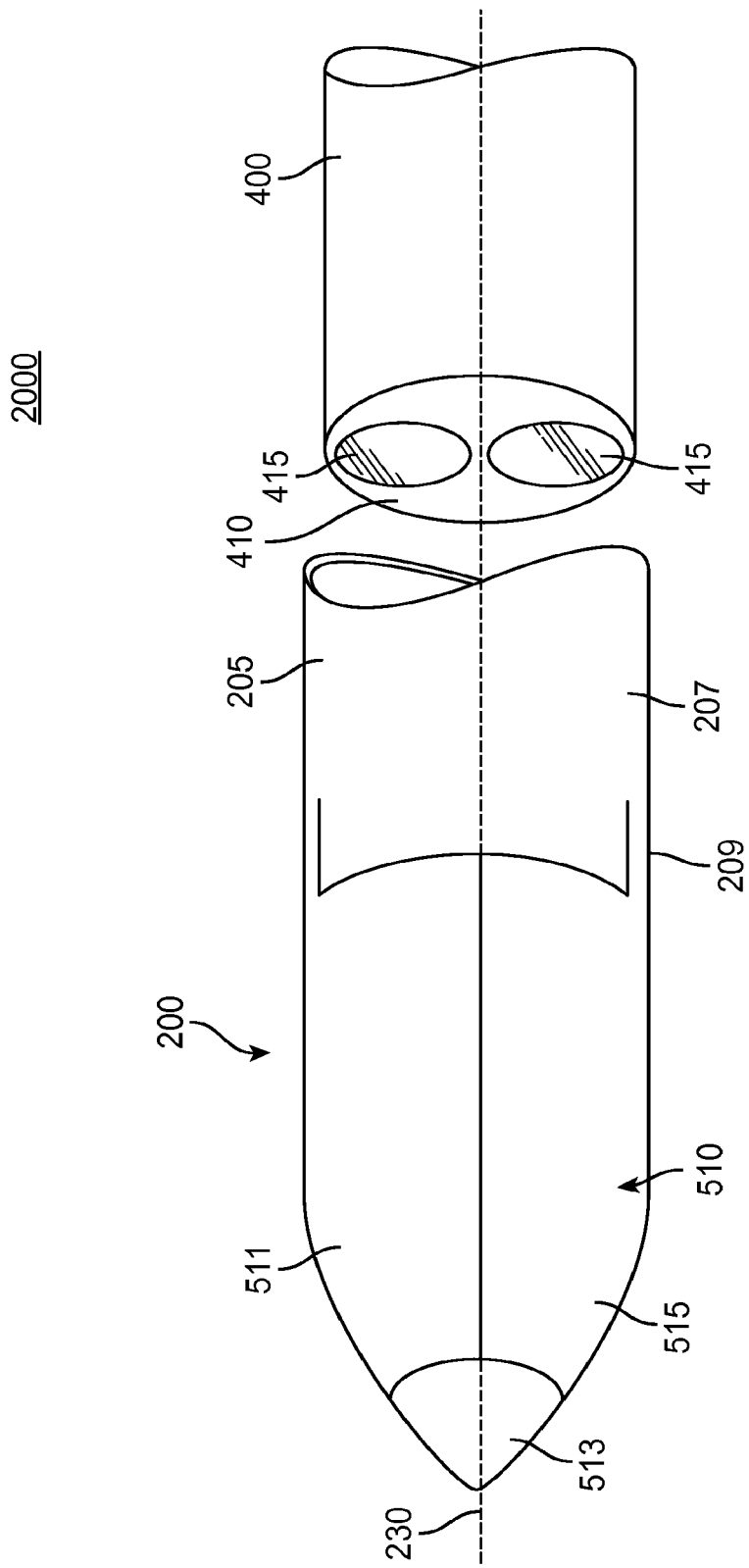
FIG. 6 is a side view of another exemplary embodiment of a jawed trocar assembly in a first position (such as a rest position) and illustrating an implement (such as an endoscope) to be inserted therein in accordance with the present disclosure.

While FIGS. 4 and 5 illustrate a trocar assembly 200 having a pair of jaws 210 which are substantially identical, in another embodiment, the pair of jaws 210 need not be identical. For example, FIG. 6 illustrates another embodiment of a trocar assembly 200 having a pair of jaws 510 has a first jaw 511 and a second jaw 515, the second jaw 510 being different from the first jaw 511. In FIG. 6, the trocar assembly 200 is in the first position 2000, wherein the first jaw 511 and second jaw 515 are each substantially parallel to the longitudinal axis 230 of the hollow elongate member 250. In FIG. 6, the first jaw 511 includes a penetrating member 513 at an end thereof. In FIG. 6, the penetrating member 513 is configured to penetrate at least one layer of body tissue. For example, the penetrating member 513 can be a substantially conical tip, as illustrated in FIG. 6, a blade, a tip having a cutting surface thereon, or any other member which can penetrate at least one layer of body tissue. In FIG. 6, the second jaw 515 does not include a penetrating member. Instead the second jaw 215 is configured to be positioned adjacent the first jaw 511 in the first position 2000 such that the penetrating member 513 extends longitudinally further than an end 517 (shown in FIG. 7) of the second jaw 515. For example, in FIG. 6, the penetrating member 513 extends longitudinally further than the end 517 of the second jaw 515 in the first position 2000 (for example the rest position) such that the exterior surfaces of the penetrating member 513 and the second end 517 form a substantially conical contour. That is, in at least one embodiment where the first jaw 511 includes a penetrating member 513, the first jaw 511 and the second jaw 515 can be configured such that in the first position 2000 (for example, the rest position), the first jaw 511 and the second jaw 515 can form a substantially contiguous contour. With the substantially contiguous contour, the trocar assembly 205 can have a substantially uniform shape that permits a clean penetration through at least one layer of body tissue. Also illustrated in FIG. 6 is an implement 400 that is an endoscope which is insertable through the hollow elongate member 205. The endoscope 400 in FIG. 6 has two lenses 415. However, in other embodiments, the endoscope 400 can have one lens 415' (shown in FIG. 9) or more than one lens 415. For example, in FIG. 9, a lens 415' of an endoscope 400 having a single lens 415' is shown overlaid on the two lenses 415.

Figure 7:
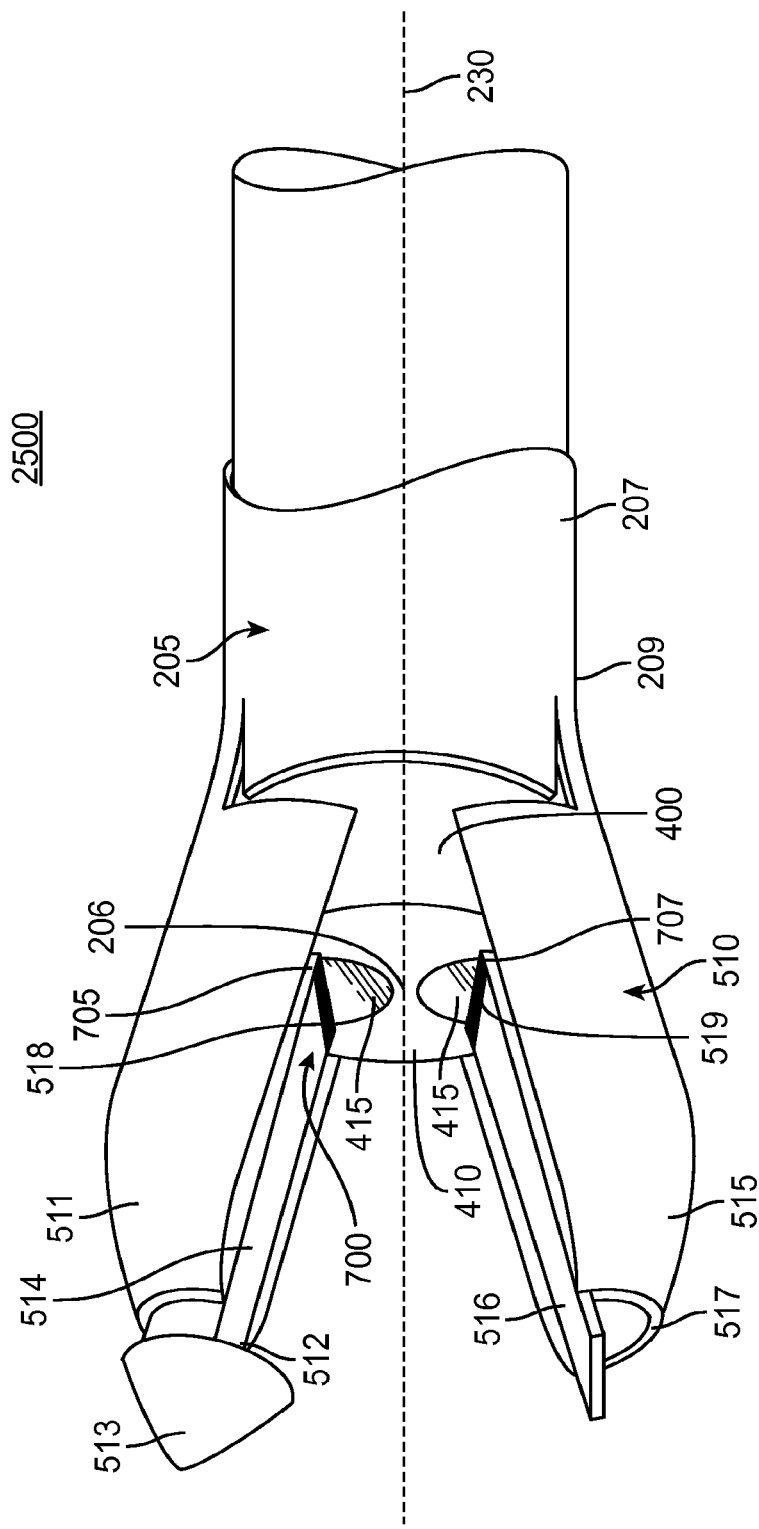
FIG. 7 is a perspective view of a side of the jawed trocar assembly illustrated in FIG. 6 except in a second position (such as an expanded position)

FIGS. 7 and 9-13 illustrate another embodiment of a trocar assembly 200 having a pair of jaws 511, 515. In FIG. 7, the trocar assembly 200 can have a first jaw 511 having a first slider 514 axially translatably coupled thereto. For example, the first slider 514 can be configured to translate along the first jaw 511 parallel to the longitudinal axis of the first jaw 511. That is, the first slide 514 can be axially translatable with respect to the first jaw 511. The longitudinal axis of the first jaw 511 can be parallel to the longitudinal axis 230 of the hollow elongate member 205. Similarly, the second jaw 515 can have a second slider 516 axially translatably coupled thereto. The second slider 516 can be configured to translate along the longitudinal axis of the second jaw 516. That is, the second slider 516 can be axially translatable with respect to the second jaw 516. The longitudinal axis of the second jaw 516 can be parallel to the longitudinal axis 230 of the hollow elongate member 205 in the first position 2000. In FIG. 7, though not illustrated, when the trocar assembly 205 is in the first position 2000 (for example, the rest position), the first slider 514 and the second slider 516 can be positioned adjacent one another parallel to the longitudinal axis 230 of the hollow elongate member 205. In at least one embodiment, the first slider 514 and the second slider 516 can be translatably coupled to their respective jaws 511, 515 via a pin and slot coupling (not shown). For example, the first slider 514 and second slider 516 can have a slot (not shown) formed therein. The slot of the first slider 514 can be configured to engage a pin (not shown) coupled to the first jaw 511. The slot of the second slider 516 can be configured to engage a pin (not shown) coupled to the second jaw 515. Thus, the pins of the first jaw 511 and second jaw 515, slide within the slots of the respective first slider 514 and second slider 516, thereby providing for the axially translatable cooperation between the jaws 511, 515, and the sliders 514, 516. Those of ordinary skill in the art will appreciate that the sliders 514, 516 can be coupled to their respective jaws 511, 515 by other couplings. For example, by a biasing coupling, a spring coupling, or other coupling that allows for the axially translatable cooperation between the sliders 514, 516 and their respective jaws 511, 515. In at least one embodiment, at least one of the sliders 514, 516 can be biased towards the first position 2000, where and end 518, 519 of the slider 514, 516 is adjacent the second end 207 of the hollow elongate member 205. For example, the slider 514, 516 can be biased by a spring, a cam surface, or other mechanism configured to bias the slider 514, 516 toward the first position 2000. In another embodiment, only one of the sliders 514, 516 can be biased towards the first position.

In the second position 2500 of the trocar assembly 200, the first slider 514 and second slider 516 are able to translate along their respective jaw 511, 515. For example, in FIG. 7, when an implement 400 is inserted and advanced through the hollow elongate member 205 such that the distal end 410 of the implement 400 engages an end 518, 519 of the first slider 514 and second slider 516. As the implement 400 is further advanced through the hollow elongate member 205 to protrude out from the second end 207 and to advance through the first jaw 511 and second jaw 515, the implement 400 can apply pressure against the first slider 514 and second slider 516 to translate the first slider 514 and second slider 516 away from the second end 207 of the hollow elongate member 205. For example, the first slider 514 and second slider 516 can translate axially away from the second end 207 of the hollow elongate member 205 as the first jaw 511 and second jaw 515 rotate radially away from the longitudinal axis 230 of the hollow elongate member 205 in the second position 2500 (for example, the expanded position). In other words, as the implement 400 is advanced through the hollow elongate member 205 and the first jaw 511 and second jaw 515, the implement 400 can assist in translating the first slider 514 and second slider 516 with respect to the first jaw 511 and second jaw 515. While FIG. 7 illustrates a trocar assembly 200 having two sliders 514, 516, those of ordinary skill in the art will appreciate that the trocar assembly 200 can have one slider 514, 516.

In the exemplary embodiment illustrated in FIG. 7, the trocar assembly 200 can include a scope cleaner 700 interiorly positioned with respect to the jaws 510. For example, in FIG. 7, the scope cleaner 700 can be a pair of wiper blades 705, 707 coupled to the jaws 510. The wiper blades 705, 707 can be rigid wiper blades, deformable wiper blades, tips of wiper blades, absorbent blades, or other structures which can wipe or sweep debris off of implements 400 insertable in the hollow elongate member 205. In FIG. 7, a first wiper 705 can be coupled to the first jaw 511. In FIG. 7, the first wiper blade 705 can be coupled to the first slider 514. In FIG. 7, the first slider 714 has the penetrating member 513 coupled to a first end 512, and the first wiper blade 705 can be coupled to the first slider 514 at an end 518 opposite to the penetrating member 513. The first wiper blade 705 can be configured to sweep across an interior 208 (shown in FIGS. 16-18) of the hollow elongate member 205 when the first slider 514 translates axially away from the second end 207 of the hollow elongate member 205 and the first jaw 511 is rotated into the second position 2500. The second wiper blade 707 can be coupled to the second jaw 515. For example, in FIG. 7, the second wiper blade 707 can be coupled to the second slider 516. In FIG. 7, the second wiper blade 707 can be coupled to an end 519 of the second slider 516, such that in the first position 2000, the first wiper blade 705 and the second wiper blade 707 are adjacent one another. The second wiper blade 709 can be configured to sweep across an interior 208 (shown in FIGS. 16-18) of the hollow elongate member 205 when the second slider 516 translates axially away from the second end 207 of the hollow elongate member 205 and the second jaw 515 is rotated into the second position 2500. The sweeping movement of the first wiper blade 705 and second wiper blade 707 will be described in further detail with the exemplary non-limiting embodiment illustrated in FIG. 9-13.

FIG. 9 illustrates a cross-sectional view of the trocar assembly 200 illustrated in FIG. 7 taken along the longitudinal axis 230 of the hollow elongate member 205. In FIG.

9, the trocar assembly 200 is in the first position 2000 (e.g., rest position). A locking member 300, such as the one illustrated in FIG. 8, is inserted in the hollow elongate member 205 and engaged with the first jaw 511 and second jaw 515 to maintain the trocar assembly 200 in the first position 2000. For example, as illustrated in FIG. 9, the tabs 810 of the locking member 300 engage recesses 509 formed in an interior surface 507 of the first jaw 511 and second jaw 515. As the locking member engages recesses 509, the first jaw 511 an second jaw 515 are prevented from rotating axially away from the longitudinal axis 230 of the hollow elongate member 205. Also illustrated in FIG. 9, as the locking member 300 maintains the trocar assembly 200 in the first position, the first wiper blade 705 and second wiper blade 705 are maintained adjacent one another and proximate to a center 206 of the cross-sectional face of the hollow elongate member 205. FIG. 9 also illustrates a cross-sectional view of the trocar assembly 200 taken along a plane perpendicular to the first jaw 511 and second jaw 515 and the longitudinal axis 230. As illustrated in this cross-sectional view, when the locking member 300 maintains the trocar assembly 200 in the first position, the first wiper blade 705 and the second wiper blade 707 are maintained such that the first wiper blade 705 and second wiper blade 707 are adjacent to one another. In the event an implement 400 is inserted in the hollow elongate member 705 and the trocar assembly 200 is in the first position 2000, the first wiper blade 705 and the second wiper blade 707 can be adjacent to a distal end 410 of the implement 400. For example, as illustrated in FIG. 9, the first wiper blade 705 and the second wiper blade 707 are disposed adjacent one another.

FIG. 10 illustrates the trocar assembly 200 in FIG. 9, except the locking member 300 has been removed from the hollow elongate member 205. As the locking member 300 has been removed, the trocar assembly 200 is permitted to transition from the first position 2000 (e.g., rest position) to the second position 2500. The trocar assembly 200 can be transitioned to the second position 2500 as the implement 400 is advanced through the hollow elongate member 205 to protrude out from the second end 207 of the hollow elongate member 205.

FIG. 11 illustrates the trocar assembly 200 in FIGS. 9 and 10, where the implement 400 has been advanced towards the second end 207 of the hollow elongate member 205 such that the implement 400 begins to protrude out from the second end 207 and the first jaw 511 and second jaw 515 begin to rotate axially away from the longitudinal axis 230 of the hollow elongate member 205. That is, FIG. 11 illustrates the trocar assembly 200 beginning to transition to the second position 2500 (e.g., expanded position). In FIG. 11, as the implement 400 advances further through the hollow elongate member 205 to protrude out from the second end 207 of the hollow elongate member 205, the first slider 514 and second slider 516 translate axially away from the second end 207 of the hollow elongate member 205, thereby permitting the wiper blades 705, 707 to sweep across the exterior surface of the implement 400. FIG. 11 also illustrates a cross-sectional view of the trocar assembly 200 taken along a plane parallel to the longitudinal axis 230. As illustrated in this cross-sectional view in FIG. 11, as the implement 400 protrudes out from the second end 207 of the hollow elongate member 205 and engages the wiper blades 705, 707, the force of the implement 400 against the wiper blades 705, 707 can cause the wiper blades 705, 707 to sweep across the exterior surface of the implement 400. For example, as illustrated in FIG. 11, the wiper blades 705, 707 can move radially away from the center 206 of the cross-sectional face of the implement 400 and the second end 207 of the hollow elongate member 205. That is, the wiper blades 705, 707 can sweep outwardly across the face of the implement 400 beginning from the center 206 of the implement 400 towards the circumference of the implement 400.

Figure 12:
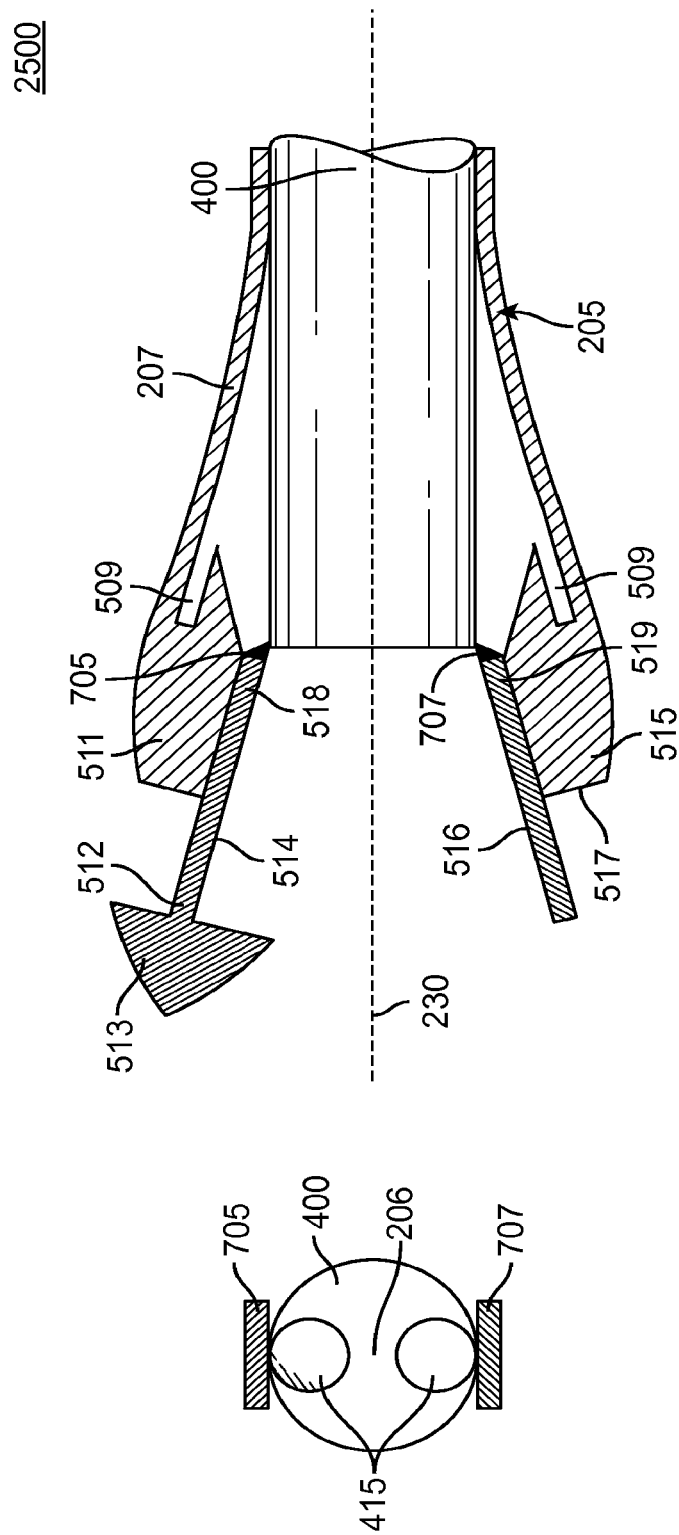

FIG. 12 illustrates the trocar assembly 200 in the second position 2500 (e.g., expanded position). In the non-limiting exemplary embodiment illustrated in FIG. 12, the implement 400 has been advanced through the hollow elongate member 205 beyond the second end 207 of the hollow elongate member 205. As illustrated in FIG. 12, the implement 400 has been advanced beyond the second end 207 of the hollow elongate member 205 such that the implement 400 can advance between the first jaw 511 and second jaw 515. As illustrated in FIG. 12, as the implement 400 is further advanced through the hollow elongate member 205 and between the first jaw 511 and second jaw 515, the wiper blades 705, 707 sweep further outwardly across the exterior face of the implement 400 until the wiper blades 705, 707 are positioned proximate the circumference of the implement. If the implement 400 is advanced even further through the hollow elongate member 205 and between the first jaw 511 and the second jaw 515, the implement 400 can be advanced to protrude beyond the second end 517 of the second jaw 515 and beyond the penetrating member 213 of the first jaw 511, as illustrated in FIG. 13.

Figure 13:
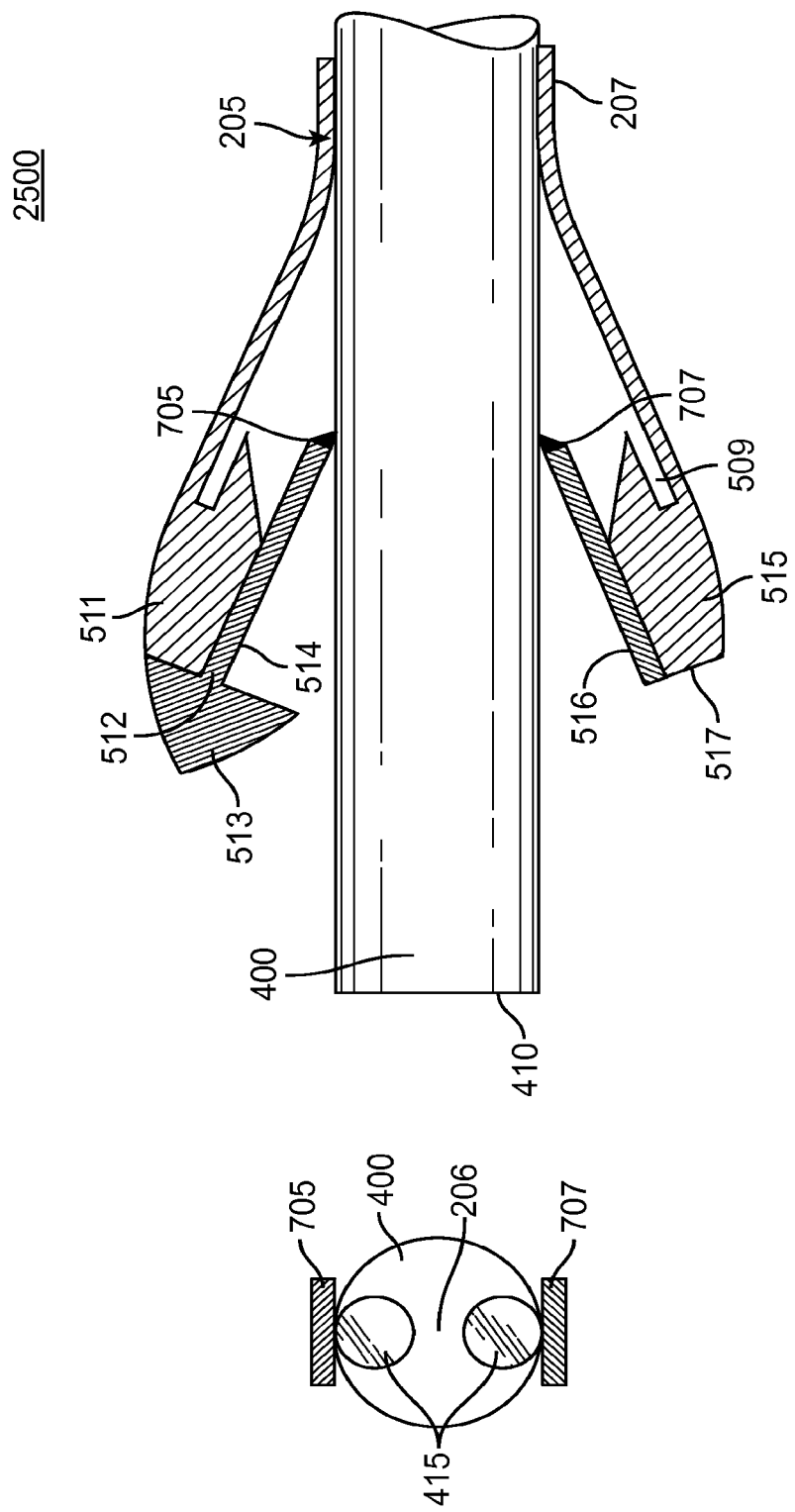

As illustrated in FIG. 13, when the implement 400 is advanced such that it protrudes beyond the second end 517 of the second jaw 515 and the penetrating member 513 of the first jaw 511, the wiper blades 705, 707 can remain positioned adjacent the circumference of the implement 400. In at least one non-limiting exemplary embodiment, as illustrated in FIG. 13, the first slider 514 and second slider 516 can be biased towards the second end 207 of the hollow elongate member 205. For example, the first slider 514 and the second slider 516 can be biased such that the first slider 514 and second slider 516 form a contiguous contour with their respective first jaw 511 and second jaw 515, as illustrated in FIG. 13. For example, each of the first slider 514 and the second slider 516 can be biased towards the second end 207 of the hollow elongate member by a biaser such as a spring, a cam surface, or other biasing member.

In FIGS. 9-13, as the wiper blades 705, 707 can be swept across the exterior of the implement 400, the wiper blades 705, 707 can wipe debris from the implement 400. For example, if the implement 400 is an endoscope, as illustrated in FIG. 9-13, the sweeping action of the wiper blades 705, 707 can wipe debris from the endoscope, thereby increasing the surgeon's visibility of the body cavity in which the endoscope is inserted to perform surgical procedures. The wiper blades 705, 707 can also reduce "fogging" of the lens of the endoscope. With the embodiment of the scope cleaner 700 illustrated in FIGS. 7 and 9-14, a surgeon need not remove the endoscope 400 from the body cavity to clean the endoscope 400. That is, the surgeon need only retract and advance the endoscope 400 from the trocar assembly 200. For example, in FIG. 13, as the endoscope 400 protrudes beyond the second end 517 of the second jaw 515 and the penetrating member 513 of the first jaw 511, the endoscope 400 can be manipulated by the surgeon during medical procedures. During these medical procedures, the endoscope 400 can accumulate debris thereon. In the event the surgeon's visibility from the endoscope 400 becomes obstructed, the endoscope 400 can be retracted within the hollow elongate member 205 such that the trocar assembly 200 is in the first position 2000 (e.g., the rest position). The endoscope 400 can then be advanced through the hollow elongate member 205 and out beyond the second end 517 of the second jaw 515 and the penetrating member 513 of the first jaw 511, thereby permitting the wiper blades 705, 707 to sweep across the exterior surface of the endoscope and to wipe debris off of the endoscope 400. As a result, the surgeon's visibility from the endoscope 400 is clearer as the endoscope 400 is cleaned by the wipers 705, 707. While FIG. 9-13 illustrate the wiper blades 705, 707 having a length that is longer than the diameter of the lenses 415, 415', those of ordinary skill in the art will appreciate that the wiper blades 705, 707 can have a length that is substantially equal to the entire diameter of the lenses 415, 415', a length that is substantially equal to an inner diameter of the hollow elongate member 205, a length that is 80 percent of the inner diameter of the hollow elongate member 205, or any other length which can clean debris off of the endoscope 400 or implement inserted into the trocar assembly.

Figure 14:
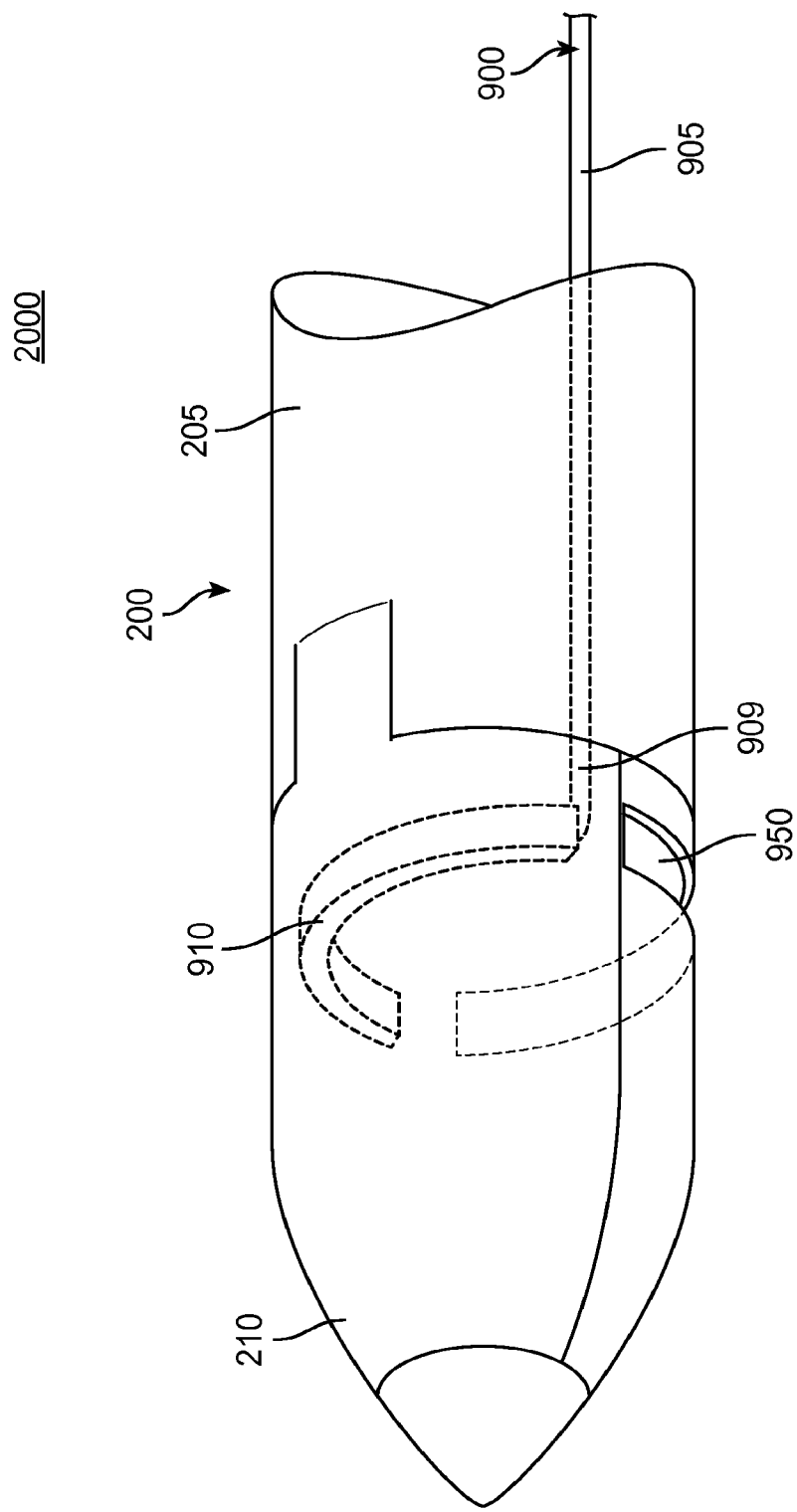
FIGS. 14 and 15 are perspective views of another exemplary embodiment of a jawed trocar assembly, in accordance with the present disclosure, having a scope cleaner mechanism which is rotatable.
Figure 15:
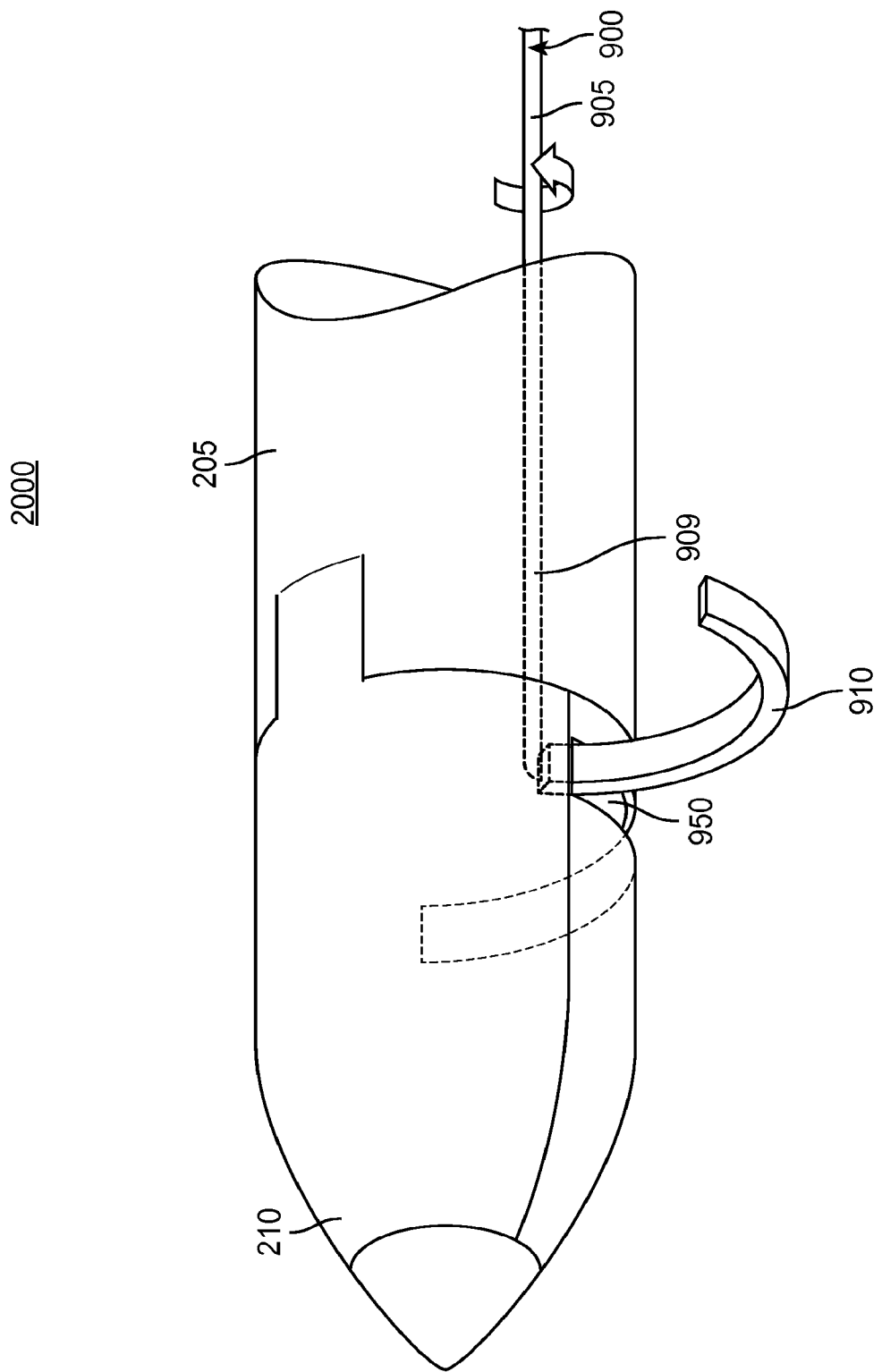

FIGS. 14 and 15 are an illustration of another non-limiting exemplary embodiment of a trocar assembly 200 of the present disclosure having an alternative embodiment of a scope cleaner 900. In FIGS. 14 and 15, the scope cleaner is a rotatable scope cleaner 900. For example, the rotatable scope cleaner 900 comprises a rotatable stem 905 and a wiper blade 910. The rotatable stem 905 can be actuated by the surgeon. The wiper blade 910 is rotatably coupled to a distal end 909 of the stem 905. For example, a rotation of the stem 905 causes the wiper blade 910 to rotate. As the wiper blade 910 rotates, the wiper blade 905 can sweep across the cross-sectional face of an implement 400 inserted into the hollow elongate member 205 and/or an interior of the hollow elongate member 205. In FIGS. 14 and 15, the wiper blade 910 is a rotatable arched blade. For example, in FIGS. 14 and 15, the at least one jaw 210 includes an aperture 950 formed therein. The aperture 950 is configured such that the rotatable wiper blade 910 can pass therethrough when the wiper blade 910 is rotated. FIG. 14 illustrates a starting position of the rotatable blade 910 where the rotatable blade 910 is positioned parallel to an interior circumference of the at least one jaw 210. When the endoscope 400 is inserted and/or retracted into the hollow elongate member 205, and the trocar assembly 200 is placed in the first position 2000 (e.g., rest position), the endoscope 400 can be positioned adjacent the rotatable wiper blade 910 such that the wiper blade 910 engages the exterior surface of the endoscope 400. The rotatable stem 905 can be actuated to rotate the wiper blade 910. For example, the wiper blade 910 can be rotated outwardly through the aperture 950, such that the wiper blade 910 is positioned externally to the at least one jaw 210. FIG. 15 illustrates an end position of the rotatable blade 910 after the rotatable stem 910 has been rotated to rotate the wiper blade 910 outwardly through the aperture 950. As the wiper blade 910 is rotated outwardly through the aperture 950, the wiper blade 910 can sweep across the exterior surface of the endoscope 400, thereby cleaning the endoscope and removing debris therefrom. In FIGS. 14 and 15, the rotatable wiper blade 910 can be arched to maximize the surface area of the endoscope cleaned or wiped by the wiper blade. However, in other embodiments, the wiper blade 910 can have other shapes and configurations, so long as the wiper blade 910 can be manipulated to clear debris from the surface of the endoscope, thereby increasing or clearing the surgeon's visibility of the endoscope 400.

Figure 16:
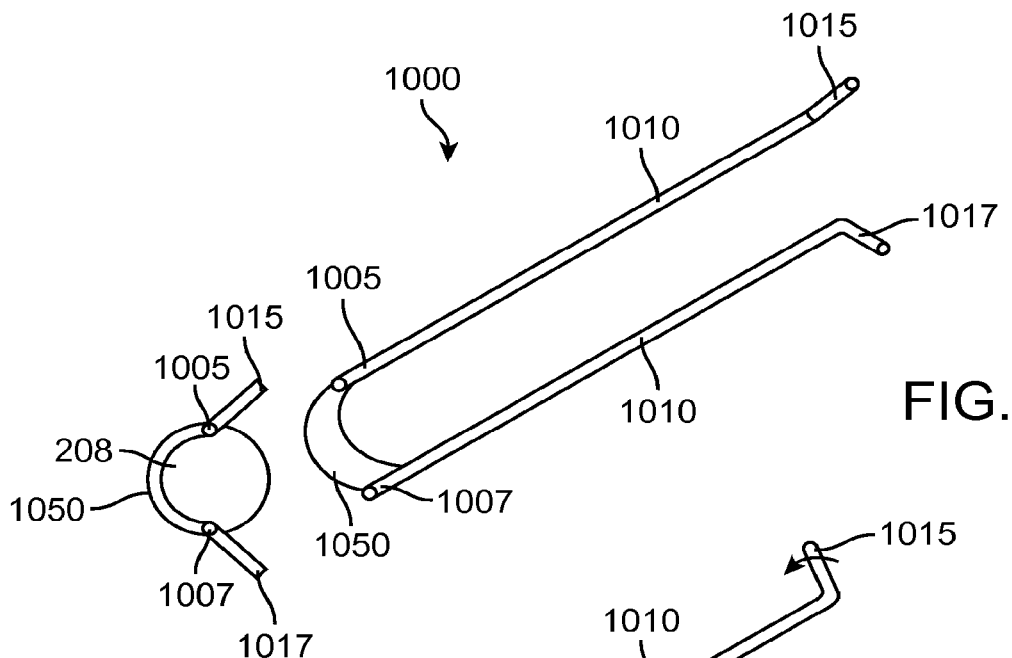
FIGS. 16-18 are perspective views of another embodiment of a scope cleaner mechanism which can be inserted into a jawed trocar assembly in accordance with the present disclosure.
Figure 17:
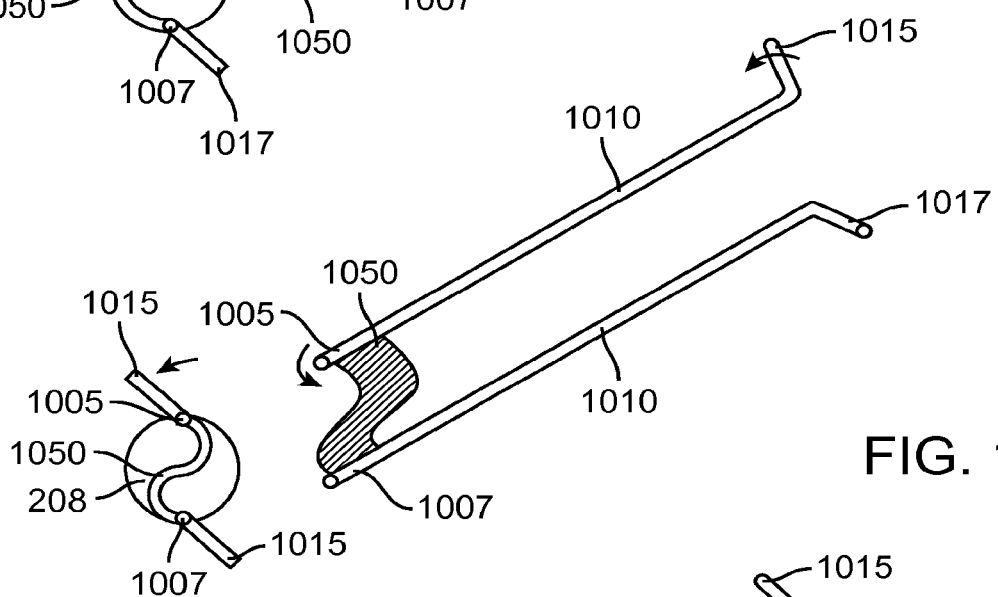
Figure 18:
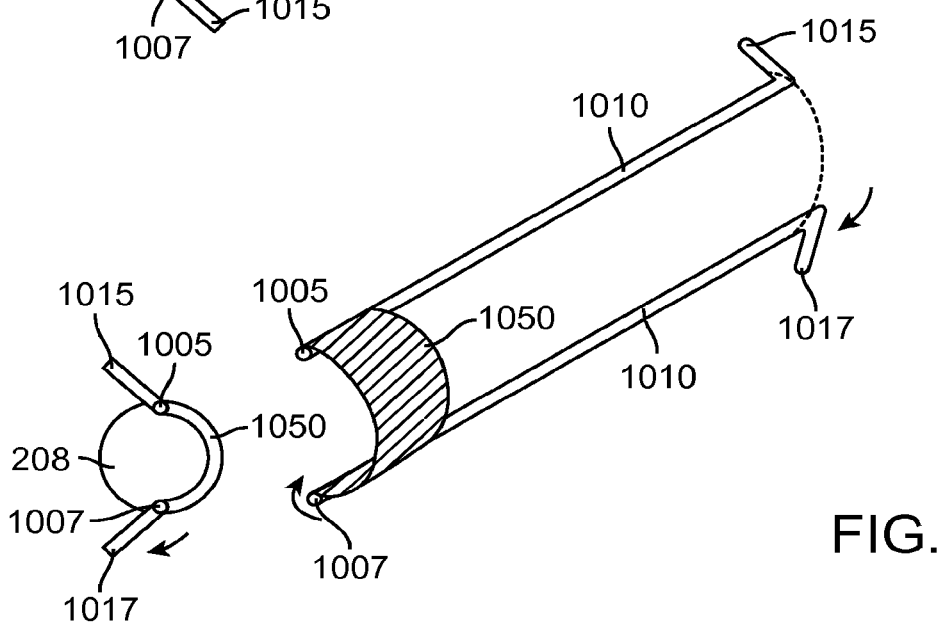

FIGS. 16-18 illustrate an alternative embodiment of a scope cleaner 1000. In FIGS. 16-18, the scope cleaner is a rotatable flexible wiper blade assembly 1000. In FIGS. 16-18, the wiper blade assembly 1000 can include a flexible wiper blade 1050 coupled to a lever 1015, 1017. The flexible wiper 1050 can be configured to be positioned between the jaw (not shown) and the second end (not shown) of a hollow elongate member (not shown) to which the flexible wiper 1050 can be coupled. In FIGS. 16-18, the flexible wiper blade 1050 can be coupled to two levers 1015, 1017. A rotation of the levers 1015, 1017 can cause the flexible wiper 2050 to sweep across an interior 208 of the hollow elongate member 205 in which the flexible wiper blade assembly 1000 is inserted. However, those of ordinary skill in the art will appreciate that the wiper blade 1050 can be coupled to only one lever.

In FIGS. 16-18, a first end 1005 of the wiper blade 1050 can be coupled to the first lever 1015. For example, in FIGS. 16-18, the first end 1005 can be coupled to the first lever 1015 by a stem 1010 configured to extend longitudinally parallel to the hollow elongate member 205 in which the flexible wiper blade assembly 1000 is inserted. The second end 1007 of the flexible wiper blade 1050 can be coupled to the second lever 1017. In at least one embodiment, such as in FIGS. 16-18, the second end 1007 of the flexible wiper blade 100 can be coupled to the second lever 1017 by a respective stem 1010 configured to extend longitudinally parallel to the hollow elongate member 205. As illustrated in FIGS. 16-18, the flexible wiper blade 1050 can extend along a diameter of the interior of a hollow elongate tube in which the flexible wiper blade assembly 1000 is inserted. In FIGS. 16-18, the flexible wiper blade 1050 extends across an entirety of the diameters to the hollow elongate member to ensure that an entirety of the cross-sectional surface of the hollow elongate member will be cleaned. However, in other embodiments, the flexible wiper blade 1050 can extend partially across the diameter of the hollow elongate member or can extend across the interior of the hollow elongate member in any other manner that allows the wiper blade 1050 to sweep across at least a portion of the interior of the hollow elongate member.

In FIGS. 16-18, a rotation of the levers 1015, 1017 can cause the flexible wiper 2050 to sweep across an interior 208 of the hollow elongate member 205 in which the flexible wiper blade assembly 1000 is inserted. For example, in FIG. 17, the first lever 1015 has been rotated counterclockwise. In response to this counterclockwise rotation of the first lever 1015, the first end 1005 of the flexible wiper blade 1050 is also rotated counterclockwise. As the second end 1007 of the flexible wiper blade 1050 has not been rotated, the flexible wiper blade 1050 deforms or flexes. For example, as illustrated in FIG. 17, the flexible wiper blade 1050 can flex and form a reverse-S-shape. As the flexible wiper blade 1050 can flex, the flexible wiper blade 1050 can sweep across approximately half of an interior 208 of the hollow elongate member 205 in which the flexible wiper blade assembly 1000 is inserted. In another embodiment, the flexible wiper blade 1050 can sweep across an exterior surface of an implement (not shown), for example, across the lens of an endoscope. In the exemplary embodiment illustrated in FIGS. 16-18, the flexible wiper blade 1050 can be flexed to sweep across the remaining half of the interior 208 of the hollow elongate member 205 upon a rotation of the second lever 1017. For example, in FIG. 18, the second lever 1017 can be rotated clockwise, which thereby rotates the second end 1007 of the flexible wiper blade 1050 to also rotate counterclockwise. As a result of this rotation, the flexible wiper blade 1050 can continue to flex. As the rotation of the first lever 1015 can cause the wiper blade 1050 to flex into a reverse-S-shape, the rotation of the second lever 1017 can cause the wiper blade 1050 to continue to flex out of the reverse-S-shape. For example, the rotation of the second lever 1017 can cause the flexible wiper blade 1050 to flex into a semi-circular shape, as illustrated in FIG. 18. In FIG. 18, the flexible wiper blade 1050 has flexed to a position that is a mirror image of the beginning position of the flexible wiper blade 1050 before either of the levers 1015, 1017 has been rotated. As illustrated in FIG. 18, the flexible wiper blade 1050 has swept across substantially an entirety of the interior 208 of the hollow elongate member 205.

Figure 19:
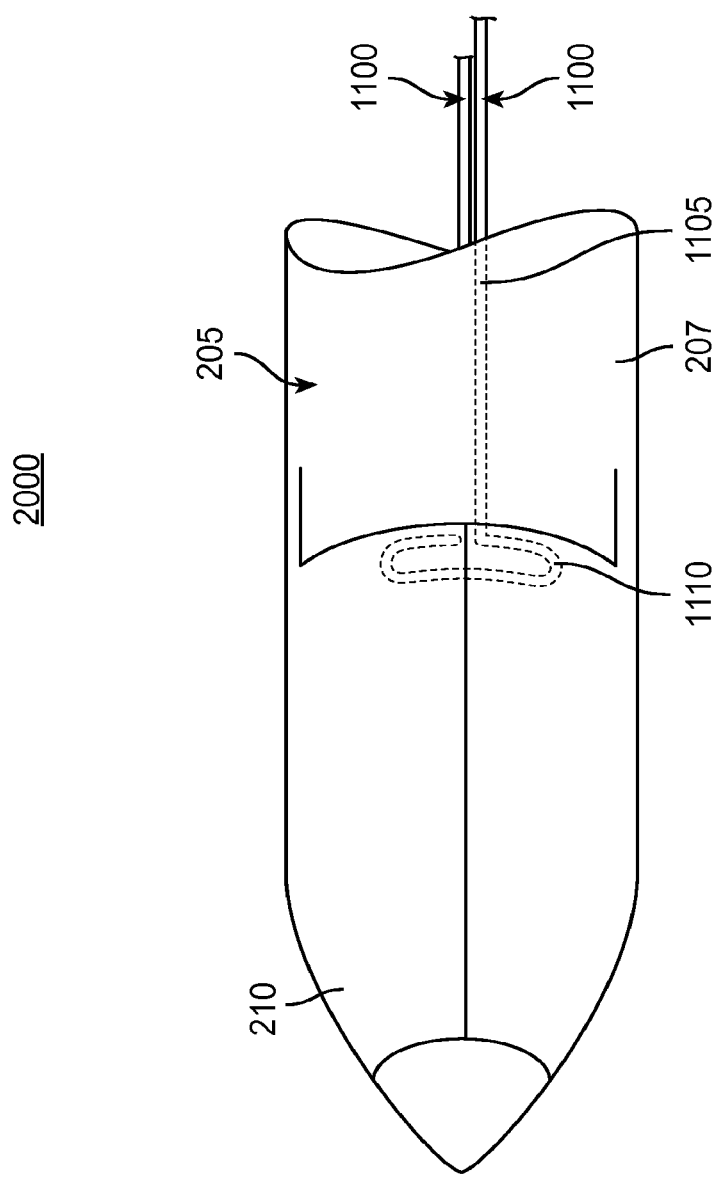
FIG. 19 is a perspective view of an exemplary embodiment of a jawed trocar assembly in accordance with the present disclosure having a biasing mechanism configured to bias the jawed trocar assembly in the second position, for example the expanded position, wherein the illustrated jawed trocar assembly is in the first position, for example, the rest position.
Figure 20:
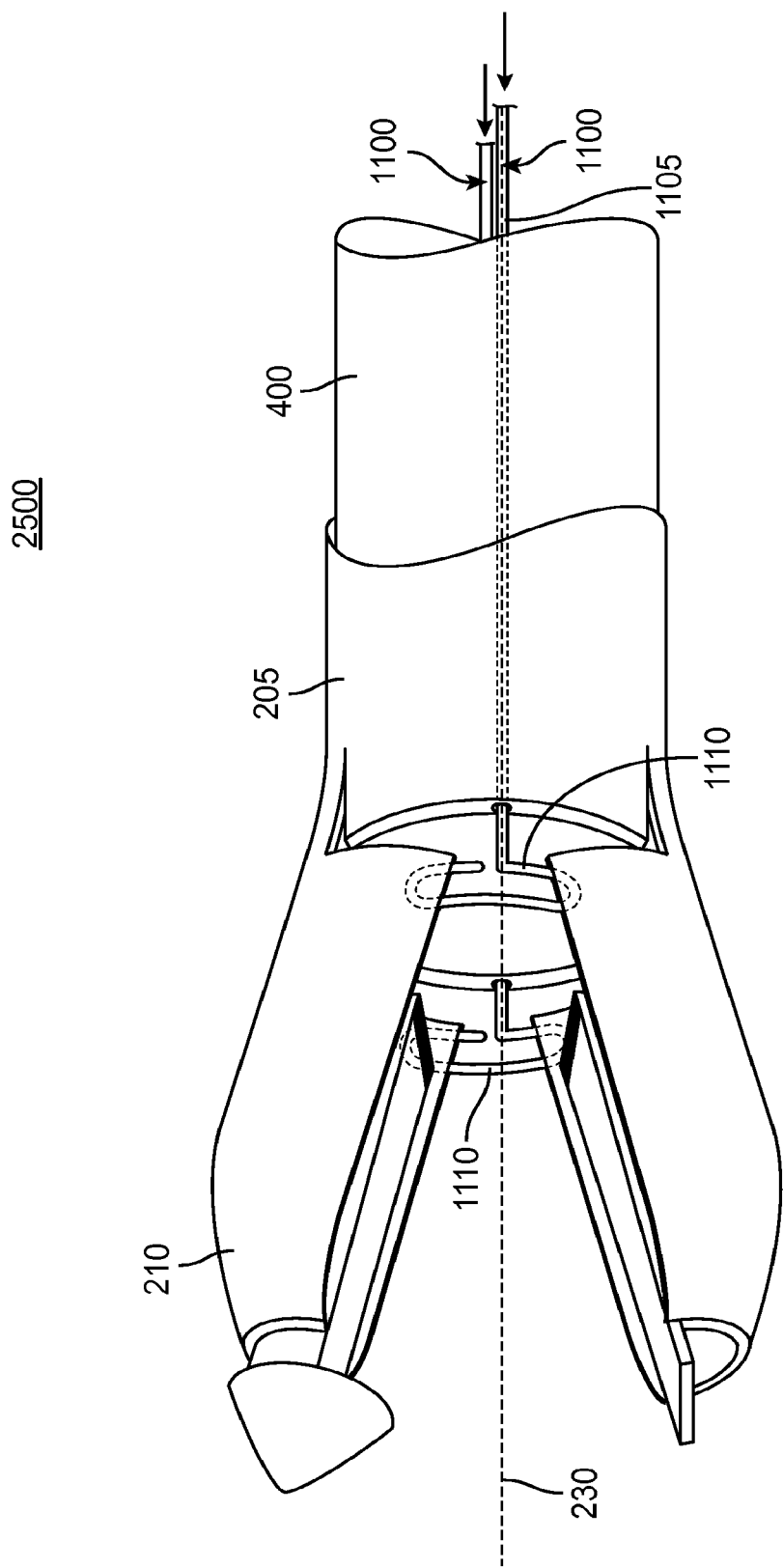
FIG. 20 is a perspective view of the jawed trocar assembly illustrated in FIG. 19, wherein the biasing mechanism has been actuated to bias the jawed trocar assembly in the expanded position.
Figure 21:
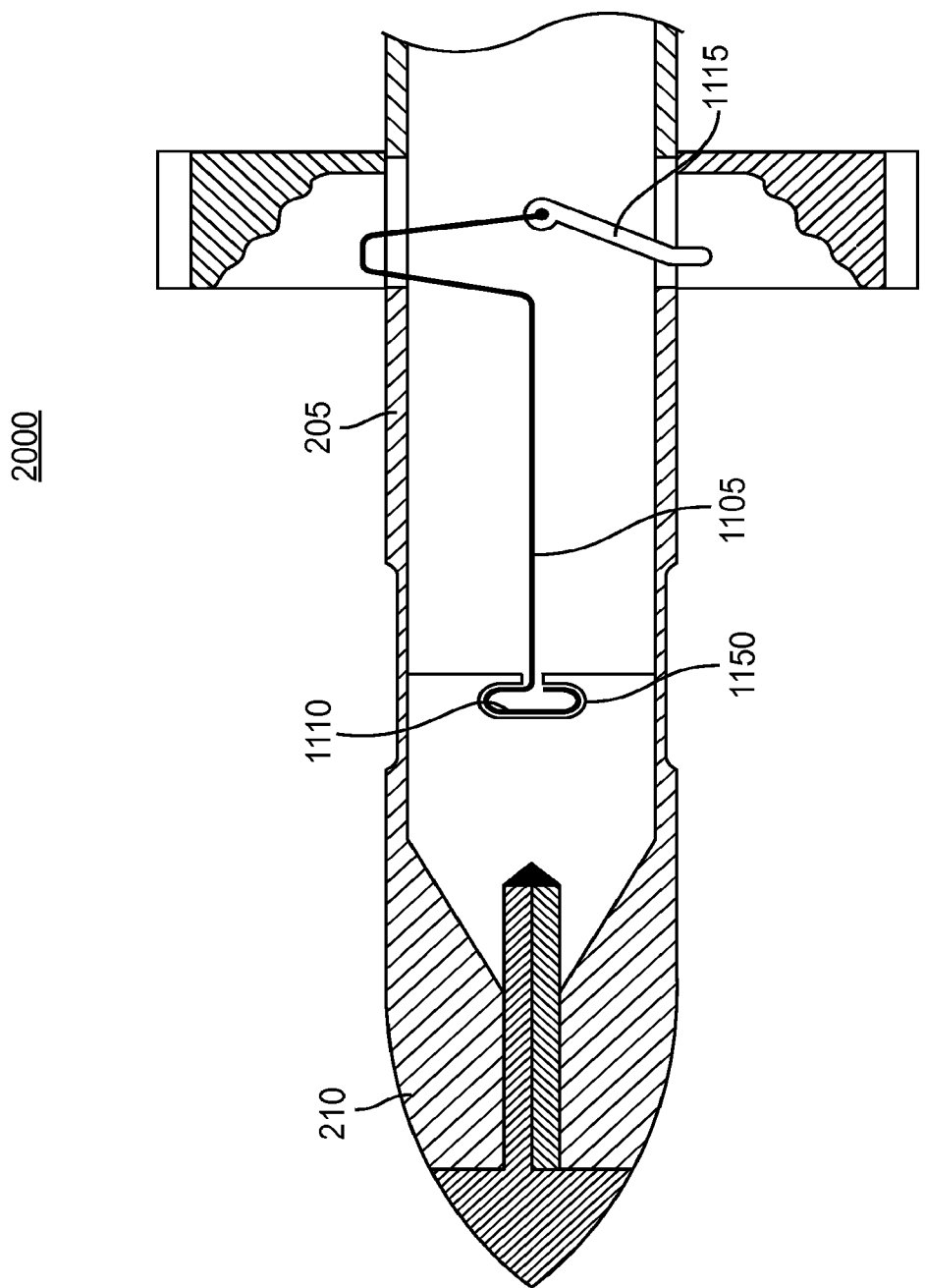
FIG. 21 is a cross-sectional view of the jawed trocar assembly illustrated in FIGS. 19 and 20 illustrating an actuator of the biasing mechanism.

FIGS. 19-21 illustrate an exemplary non-limiting embodiment of a trocar assembly 200 having a biasing mechanism 1100. The biasing mechanism 1100 can be configured to maintain the trocar assembly 200 in the second position 2500. For example, the biasing mechanism 1100 can maintain the at least one jaw 210 of the trocar assembly 200 in a position where the end 213 of the jaw is positioned radially away from the longitudinal axis (for example, a longitudinal center line) of the hollow elongate member 205. By biasing the trocar assembly 200 in the second position 2500 (e.g., the expanded position), implements 400 (not shown) can be inserted and removed during medical procedures performed within the body cavity without having to continually transition the at least one jaw 210 between the first position 2000 and the second position 2500. As the trocar assembly 200 can be biased in the second position 2500 after being inserted into the body cavity of the patient, there can be fewer moving parts within the body cavity and less irritation to the interior of the body cavity.

Those of ordinary skill in the art will appreciate that the scope cleaners 700, 900, 1000 illustrated in FIGS. 6-16 can be removably coupled to the trocar assembly 200. For example, with the scope cleaner 700 illustrated in FIGS. 9-13, the scope cleaner 700 can be detachable from the jaw 210. In other embodiments, the scope cleaners can be removably insertable from the hollow elongate member 205.

While FIG. 6-16 illustrate scope cleaners 700, 900, 1000 that include a wiping blade mechanism, those of ordinary skill in the art will appreciate that other scope cleaners can be implemented. For example, the scope cleaner can include a cleaning spray 590 (for example, as illustrated in FIG. 5). The cleaning spray 590 can include a fluid line 591, 592 connected to an actuator (not shown), which when actuated sprays fluid from the fluid line 591, 592. The fluid can be a liquid or a gas. The fluid can be a cleaning fluid or a drying fluid. In FIG. 5, the cleaning spray includes two fluid lines 591, 592. However, those of ordinary skill in the art will appreciate that one fluid line can be used or more than two fluid lines can be used. In FIG. 5, one of the fluid lines 591 can spray a cleaning fluid onto a lens of an endoscope inserted in the trocar assembly 200. The other fluid line 592 can spray a drying fluid onto the lens of the endoscope.

Those of ordinary skill in the art will also appreciate that the scope cleaner can be offset laterally or rotated on a hinge offset from the at least one jaw 210 to position the scope cleaner away from the path of an implement 400 inserted into the trocar assembly 200.

In FIGS. 19-21 the biasing mechanism 1100 includes a rod 1105 and a bias loop 1110. The bias loop 1110 can be a rigid wire shaped to conform to a recess 1150 (shown in FIG. 21) formed within a wall of the at least one jaw 210 the at least one jaw 210 of the trocar assembly 200. In FIGS. 19-21, the bias loop 1110 has an oblong shape; however, those of ordinary skill in the art will appreciate that the bias loop 1110 can have other shapes. Some examples of other shapes include a wedge like shape or a round disk like shape. In FIGS. 19-21, the bias loop 1110 has a first end configured to engage a first recess of the at least one jaw 210 the at least one jaw 210. The bias loop 1110 can also have a second end configured to engage a second recess of the at least one jaw 210. As illustrated in FIG. 21, the recess 1150 can be formed in an outer wall of the at least one jaw 210. The recess 1150 can have a rounded shape to accommodate a rounded portion of the bias loop 1110. However, those of ordinary skill in the art will appreciate that the recess 1150 can have any other shape, so long as the recess 1150 can accommodate the bias loop 1110.

In FIGS. 19-21, the bias loop 1110 can have pressure applied thereto to urge the at least one jaw 210 of the trocar assembly 200 towards the second position 2500 and maintain the trocar assembly 200 there. For example, as illustrated in FIG. 21, the bias loop 1110 can be coupled to an actuator 1115. For example, the actuator 1115 can be a lever, a knob, a dial, or any other actuator which can be actuated to place pressure onto the bias loop 1110. In FIG. 21, the bias loop 1110 is coupled to the actuator 1115 by a substantially rigid wire; however, in other embodiments, the bias loop 1110 can be coupled to the actuator by a rod, a stem, or other member which can transfer pressure from the actuator 1115 to the bias loop 1110. As illustrated in FIGS. 19-20, when the actuator 1115 is actuator, pressure is placed on the bias loop 1110, which thereby places pressure against the interior of the recess 1150 of the jaw. As pressure is placed against the interior of the recess 1150, the at least one jaw 210 can be rotated from the first position 2000, illustrated in FIG. 19, to the second position 2500, illustrated in FIG. 20. When the actuator 1115 is maintained in a position that constantly applies pressure to the bias loop 1110, the trocar assembly 200 can be maintained in the second position 2500 (e.g., expanded position). When the actuator 1115 is released from the position that applies pressure to the bias loop 1110, pressure is removed from the bias loop 1110, and the at least one jaw 210 can be transitioned back to the first position 2000 (e.g., rest position) illustrated in FIG. 19. FIGS. 19-21 illustrate a biasing mechanism 1100 that includes two biasing loops 1110; however, those of ordinary skill in the art will appreciate that the trocar assembly 200 can have fewer or more than two loops 1110. Additionally, while FIGS. 19-21 illustrate a biasing mechanism 1100 that includes an actuator 1115 and a biasing loop 1100, those of ordinary skill in the art will appreciate that other biasing mechanisms 1110 can be utilized to maintain the trocar assembly 200 in the second position 2500. For example, the biasing mechanism 1100 can be a plug, a stopper, or other mechanism which can bias the trocar assembly in the second position 2500.

Figure 22:
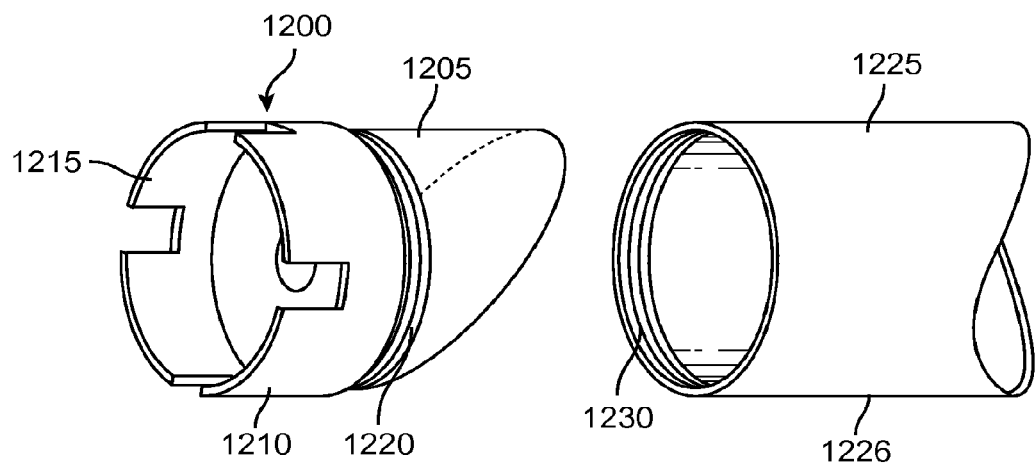
FIG. 22 is a perspective view of a reflecting member.
Figure 23:
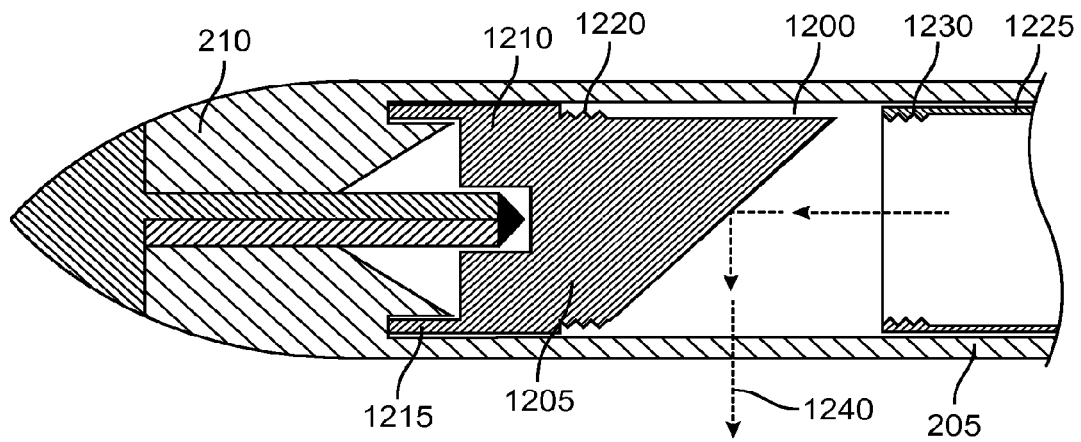
FIG. 23 is a cross-sectional view of the reflecting member assembled with a jawed trocar assembly in accordance with an exemplary embodiment.

In at least one embodiment, the jawed trocar assembly 200 can include a reflecting member 1200, as illustrated in FIGS. 22 and 23. The reflecting member 1200 can allow for a radial view by an endoscope (not shown) inserted therein. For example, an endoscope can be inserted into the jawed trocar assembly to provide an axial view of the body cavity into which the jawed trocar assembly 200 is inserted. However, in some instances, the optics looking axially can be difficult due to shallow angles and reflections. A reflecting member 1200, for example, as illustrated in FIG. 22, can enhance the views provided by the endoscope. For example, the reflecting member 1200 can have a reflective surface which can reflect an image of the body cavity or the incision surface of the body tissue to be penetrated to an endoscope inserted into the jawed trocar assembly. That is, the body cavity or body tissue to be penetrated which is radially adjacent to the jawed trocar assembly 200 when the jawed trocar assembly 200 is inserted in the body cavity can be reflected via the reflecting member 1200 to the endoscope inserted in the hollow elongate member 205 of the jawed trocar assembly 200.

FIG. 22 illustrates an exemplary embodiment of such a reflecting member 1200. In FIG. 22, the reflecting member 1200 can be a cylindrical member sized to fit within the hollow elongate member 205 of the jawed trocar assembly 200. The reflecting member 1200 can have a reflective portion 1205 which can reflect an image of the area radially adjacent to the trocar assembly 200 to an endoscope inserted in the hollow elongate member 205. For example, the reflective portion 1205 can be a mirror. As illustrated in FIG. 22, the reflective portion 1205 can have an angled surface (not labeled) to further enhance the radial view of the endoscope. For example, the angled surface can be angled: forty-five degrees along the diameter of the reflective portion 1205 (as illustrated in FIG. 22), sixty-degrees along the diameter of the reflective portion 1205, forty-degrees along the diameter of the reflective portion 1205, forty-five degrees along a radius of the reflective portion 1205, forty-five degrees along a portion of the diameter of the reflective portion 1205, or any other along the reflective portion 1205 so long as areas radially adjacent to the trocar assembly 200 can be reflected axially into the hollow elongate member 205 to an endoscope inserted therein. As the angled surface of the reflective portion 1205 can reflect images of areas radially adjacent to the trocar assembly to an endoscope axially inserted therein, information about the penetration and breakthrough areas of the body cavity and body tissue can be readily viewed by the operator of the endoscope.

The reflecting member 1200 can have a locking portion 1210 coupled thereto, as illustrated in FIGS. 22 and 23. In FIG. 22, the locking portion 1210 can be a hollow cylindrical member formed on a side of the reflecting member 1200 opposite to the reflective portion 1205. The locking portion 1210 can be configured to lock the jaws 210 of the trocar assembly 200 in the first position 2000 (for example, the resting position). The locking portion 1210 can operate similar to the locking member 300 discussed above. In FIGS. 22 and 23, at least one locking tab 1215 is formed on the locking portion 1210. For example, in FIG. 22, four locking tabs 1215 are formed on a circumference of the locking portion 1210. However, those of ordinary skill in the art will appreciate that there can be fewer or more locking tabs 1215 than as illustrated in FIG. 22. Those of skill in the art will also appreciate that the locking tabs 1215 can be locking feet, locking posts, locking pegs, or other locking members configured to engage a recess of the trocar assembly 200 to maintain the at least one jaw 210 in the rest position 2000.

In FIGS. 22 and 23, the reflecting member 1200 can include a placement tool 1225. The placement tool 1225 can be releasably couplable to the reflecting member 1200 to insert the reflecting member 1200 in the hollow elongate member 205 of the trocar assembly. In FIGS. 22 and 23, the placement tool 1225 can be a hollow member 1226 in which the reflecting member 1200 can be received. For example, in FIG. 22, the reflective portion 1205 can include a threaded portion 1220 configured for mating engagement with a respective threaded portion 1230 formed on the placement tool 1225. Those of ordinary skill in the art will appreciate that the reflective portion 1205 can be releasably couplable to the placement tool 1225 by other mechanism such as a snap-fitting, a conformance fitting, a twist-and-release fitting, or other releasable coupling.

When the reflecting member 1200 is to be inserted into the trocar assembly 200, the reflecting member 1200 can be coupled to the placement tool 1225 prior to inserting the reflecting member 1200 into the trocar assembly. For example, the threaded portion 1220 of the reflective portion 1205 of the reflecting member 1200 can be matingly threaded to the threaded portion 1230 of the placement tool 1225, thereby securing the reflecting member 1200 to the placement tool 1225. The placement tool 1225 can then be inserted into the hollow elongate member 205 of the trocar assembly 200 and advanced therethrough until the locking portion 1215 of the reflecting member 1200 engages the at least one jaw 210 of the trocar assembly 200 to lock the trocar assembly 200 in the rest position 2000. The placement tool 1225 can disengage the reflective portion 1205. For example, as illustrated in FIG. 23, the placement tool 1225 can disengage the reflective portion 1205 by rotating the placement tool 1225 in a direction that unmates the threaded portion 1230 of the placement tool 1225 from the threaded portion 1220 of the reflecting member 1200. When the placement tool 1225 is disengaged from the reflecting member 1200, the placement tool 1225 can be removed from the hollow elongate member 205 of the trocar assembly 200. The reflecting member 1200 can remain inside the hollow elongate member 205. In FIG. 23, the hollow elongate member 205 can have optically semi-transparent walls. For example, the hollow elongate member 205 can be clear, transparent, semi-transparent, or otherwise see-through so that images of areas adjacent to the hollow elongate member 205 can be reflected by the reflective surface 1205 of the reflecting member 1200. In FIG. 23, in the event an endoscope or other camera implement is inserted in the hollow elongate member, the reflective portion 1205 can reflect images of areas adjacent to the hollow elongate member 205 to the endoscope or camera implement. For example, as shown in FIG. 23, the reflected images can follow the radial viewing path 1240. When the trocar assembly 200 is to be transitioned into the expanded position (for example, as illustrated in FIG. 20), the placement tool 1225 can be inserted into the hollow elongate member 205, can matingly engage the reflecting member 1200, and can be removed from the hollow elongate member 205, thereby permitting the at least one jaw 210 of the trocar assembly 200 to transition into the expanded position.

The reflecting member 1200 thereby enables the camera implement to transmit an image reflected by the reflecting member 1200 to the operator of the camera implement. Thus, with the reflecting member 1200 and the camera implement, the operator of the trocar assembly can receive: enhanced views of the body tissue to be penetrated by the trocar assembly 200 and side views and radial views of the interior of the body cavity when the trocar assembly 200 is inserted therein.

While the FIGS. 1-23 illustrate a jawed trocar assembly in which the at least one jaw 210 is formed on or permanently coupled to the hollow elongate member 205, those of ordinary skill in the art will appreciate that the at least one jaw 210 can be releasably coupled to the hollow elongate member 205. For example, the at least one jaw 210 and the end of the hollow elongate member 205 to which the at least one jaw 210 can have corresponding threaded engagement portions. That is, the at least one jaw 210 can be releasably coupled to the hollow elongate member 205 by screwing the at least one jaw 210 to the hollow elongate member 205. In other embodiments, the at least one jaw can 210 can be releasably coupled to the hollow elongate member 205 by a snap-fit engagement or any other releasable coupling. By having a releasably couplable at least one jaw 210, the jaw 210 can be disposable or reusable. The jaw 210 can also be configured to fit existing trocar members, disposable trocars, or other hollow elongate member. In another embodiment, the hollow elongate member 205 can have a slit extending parallel to the longitudinal axis of the hollow elongate member 205 and extending along a majority of the longitudinal axis. For example, the slit can extend along 30 percent, 50 percent, 75 percent, or any other majority of the longitudinal axis.

While FIGS. 1-23 illustrate a pair of jaws having symmetric jaws, those of ordinary skill in the art will appreciate that the jaws need not be symmetrical. For example, the jaws can be asymmetrical with respect to each other. That is, one jaw can have a greater surface area than the other, one jaw can be larger in size as compared to the other, one jaw can have a contour different from the other jaw, or one jaw can be otherwise different from the other jaw.

A method of inserting an endoscopic tool assembly into a body cavity, where the endoscopic tool assembly includes any one of the trocar assemblies 200 described herein and illustrated herein, can include making an incision through a first body tissue. The trocar assembly can be inserted into the incision. The trocar assembly 200 can be advanced through the incision such that the at least one jaw 210 of the trocar assembly 200 engages a second body tissue. The trocar assembly 200 can be urged against the second body tissue to penetrate through the second body tissue. The endoscopic tool can be inserted through the trocar assembly 200. The endoscopic tool can be advanced through the trocar assembly 200 beyond the second end 207 of the elongate hollow member 205, thereby transitioning the trocar assembly 200 from the rest position 2000 to the expanded position 2500. The endoscopic tool can be extended beyond the end 213 of the at least one jaw 210.

In at least one embodiment, a locking member 300 can be inserted through the trocar assembly 200 prior to inserting the trocar assembly 200 through the incision. This can thereby ensure that the at least one jaw 210 is rigid enough to penetrate through the second layer of body tissue. The locking member 300 can be removed from the trocar assembly 200 after the trocar assembly 200 has been advanced to penetrate the second body tissue, thereby allowing for the insertion of the endoscopic tool or any other implement 400 to be used for medical procedures within the body cavity.

A method of cleaning an endoscopic tool assembly inserted into a body cavity, where the endoscopic tool assembly includes any one of the trocar assemblies 200 having a scope cleaner described and illustrated herein, can include urging the trocar assembly 200 against a body tissue to penetrate through the body tissue. An endoscopic camera of the endoscopic tool can be inserted though the trocar assembly 200. The endoscopic camera can be advanced through the trocar assembly 200 beyond the second end of the elongate hollow member, thereby transitioning the trocar assembly from the rest position 2000 to the expanded position 2500. The endoscopic camera can be extended beyond the end 213 of the at least one jaw 210 to expose the lens 415 of the endoscopic camera 400 to the body cavity. In the event the lens 415 of the camera becomes dirty or accumulates debris that impedes the visibility of the surgeon during the medial procedure, the endoscopic camera 400 can be retracted into the elongate hollow elongate member 205 of the trocar assembly 200. This can thereby transition the trocar assembly 200 from the expanded position 2500 to the rest position 2000. The lens 415 can engage with the scope cleaner of the trocar assembly 200 thereby cleaning debris off of the lens 415. The endoscopic camera 400 can be reciprocated within the elongate hollow member 205 such that the lens 415 is reciprocated between being exterior to the end 213 of the at least one jaw 210 and being interior to the at least one jaw 210 and engaged with the scope cleaner.

In another embodiment, the endoscopic camera 400 can be rotated within the hollow elongate member 205 after the endoscopic camera 400 has been retracted into the hollow elongate member 205 and after the lens 415 has been engaged with the scope cleaner. The rotations of the endoscopic camera 400 can cause the scope cleaner to wipe debris off of the lens 415.

In yet another embodiment, the endoscopic camera 400 can be cleaned by actuating a lever of the scope cleaner after the lens 415 has been engaged with the scope cleaner. The actuation of the lever can cause a wiper of the scope cleaner to undulate across the surface of the lens to wipe debris of the lens. In another exemplary embodiment, actuating a lever of the scope cleaner after the lens has been engaged with the scope cleaner can cause a spray of a cleaning fluid against the lens. For example, the cleaning fluid can be a liquid, a gas, or can include both liquid and gas. For example, the scope cleaner can include two lines of cleaning fluid positioned interiorly adjacent to the end of the jaw, and actuating the lever can spray the cleaning fluid from each of the two lines. However, those of skill in the art will realize that there may be fewer or more lines of cleaning fluid for cleaning a lens.

Exemplary implementations have been described hereinabove regarding a jawed trocar assembly and a method of using the same. One of ordinary skill in the art will also appreciate that the elements and features illustrated in the implementations described and illustrated in the figures herein can be optionally included to achieve the benefits of the presently disclosed jawed trocar assembly. Additionally, those skilled in the art will appreciate that features in each of the figures described herein can be combined with one another and arrange to achieve the described benefits of the presently disclosed jawed trocar assembly. Various modifications to and departures from the disclosed implementations will occur to those having skill in the art. The subject matter that is intended to be within the spirit of this disclosure is set forth in the following claims.

What is claimed is:

1. A tip assembly comprising:
   a member having a first end and a second end, the first end being open and through which an implement is insertable;
   a pair of jaws hingedly coupled to the second end of member, wherein the pair of jaws has at least a rest position wherein at least a first jaw of the pair of the jaws is substantially parallel to a longitudinal axis of the member and an expanded position wherein the first jaw is rotated so that an end of the first jaw is positioned radially away from the longitudinal axis;
   each jaw of the pair of jaws hingedly coupled opposite one another;
   a first slider coupled to the first jaw, such that the first slider is axially translatable with respect to the first jaw;
   a penetrating member at a first end of the first slider, the penetrating member configured to penetrate at least one layer of body tissue; and
   a first scope cleaner coupled to a second end opposite to the first end of the first slider, the first scope cleaner being configured to sweep across an interior of the hollow elongate member when the first slider translates axially away from the second end of the first scope cleaner.

2. The tip assembly of claim 1, wherein the pair of jaws is adapted to penetrate through at least one layer of body tissue.

3. The tip assembly of claim 1, wherein the pair of jaws comprises a penetrating surface adapted to penetrate through at least one layer of body tissue.

4. The tip assembly of claim 1, wherein each jaw of the pair of jaws is substantially parallel to the longitudinal axis of the hollow elongate member and each is positioned with respect to other such that ends of the jaws form a substantially conical contour adapted to penetrate through the at least one layer of body tissue.

5. The tip assembly of claim 1, wherein the pair of jaws comprises:
the first jaw; and
a second jaw hingedly coupled to the second end of the member opposite the first jaw;
wherein in the rest position, the first jaw and the second jaw are each substantially parallel to the longitudinal axis of the member and wherein the penetrating member of the first jaw extends longitudinally further than an end of the second jaw.

6. The tip assembly of claim 5, wherein:
the second jaw comprises a second slider having a second scope cleaner coupled to an end thereof that is axially translatable with respect to the second jaw;
the second slider being coupled to the second jaw such that in the rest position, the first scope cleaner and the second scope cleaner are adjacent one another; and
the second scope cleaner being configured to sweep across an interior of the member when the second slider translates axially away from the second end of the first scope cleaner.

7. The tip assembly of claim 5, wherein:
the penetrating member is a substantially conical tip; and
in the rest position, the first jaw and the second jaw are positioned with respect to one another such that the substantially conical tip extends beyond the end of the second jaw, and the first jaw and the second jaw form a substantially contiguous contour.

8. The tip assembly of claim 1 further comprising a locking member insertable through the member.

9. The tip assembly of claim 8, wherein the locking member is a hollow cylindrical member comprising at least one tab at an end of the hollow cylindrical member, the at least one tab is adapted to maintain the trocar assembly in the rest position.

10. The tip assembly of claim 9, wherein the locking member is removable from the member.

11. The tip assembly of claim 1, wherein the first scope cleaner is a wiper blade coupled to the jaw such that in the rest position, the wiper blade is substantially adjacent to the second end of the hollow elongate member.

12. The tip assembly of claim 1, wherein the first scope cleaner comprises a deformable wiper blade.

13. The tip assembly as recited in claim 1, further comprising a biasing mechanism configured to bias the pair of jaws from the expanded position toward the rest position.

14. A method of cleaning an endoscopic camera inserted into a body cavity, the endoscopic tool assembly comprising inserted into a tip assembly comprising a member having a first end and a second end, a pair of jaws hingedly coupled to the second end of the member, wherein the pair of jaws has at least a rest position wherein at least a first jaw of the pair of the jaws is substantially parallel to a longitudinal axis of the member and an expanded position wherein the first jaw is rotated so that an end of the first jaw is positioned radially away from the longitudinal axis; each jaw of the pair of jaws hingedly coupled opposite one another; a first slider coupled to the first jaw, such that the first slider is axially translatable with respect to the first jaw; a penetrating member at a first end of the first slider, the penetrating member configured to penetrate at least one layer of body tissue; and a first scope cleaner coupled to a second end opposite to the first end of the first slider, the first scope cleaner being configured to sweep across an interior of the hollow elongate member when the first slider translates axially away from the second end of the first scope cleaner, the method comprising:
urging a trocar assembly against a body tissue to penetrate through the body tissue;
inserting the endoscopic camera through the trocar assembly;
advancing the endoscopic camera through the trocar assembly beyond the second end of the member, thereby transitioning the trocar assembly from the rest position to the expanded position;
extending the endoscopic camera beyond the end of the jaw to expose a lens of the endoscopic camera to the body cavity;
retracting the endoscopic camera into the member, thereby transitioning the trocar assembly from the expanded position to the rest position;
engaging the lens with the scope cleaner, thereby cleaning debris off of the lens.

15. The method of claim 14 wherein engaging the lens with the scope cleaner comprises:
reciprocating the endoscopic camera within the member such that the lens is reciprocated between being exterior to the end of the jaw and being interior to the jaw and engaged with the scope cleaner.

16. The method of claim 15 further comprising:
rotating the endoscopic camera within the member after the endoscopic camera has been retracted into the elongate member and after the lens has been engaged with the scope cleaner, the rotations of the endoscopic camera causing the scope cleaner to wipe debris off of the lens.

* * * * *